(12) United States Patent
de la Huerga

(10) Patent No.: US 6,820,093 B2
(45) Date of Patent: Nov. 16, 2004

(54) METHOD FOR VERIFYING RECORD CODE PRIOR TO AN ACTION BASED ON THE CODE

(75) Inventor: Carlos de la Huerga, Milwaukee, WI (US)

(73) Assignee: HyperPhrase Technologies, LLC, Madison, WI (US)

(*) Notice: Subject to any disclaimer, the term of this patent is extended or adjusted under 35 U.S.C. 154(b) by 0 days.

(21) Appl. No.: 10/307,734

(22) Filed: Dec. 2, 2002

(65) Prior Publication Data

US 2003/0131024 A1 Jul. 10, 2003

Related U.S. Application Data

(63) Continuation-in-part of application No. 09/247,349, filed on May 3, 1999, which is a continuation-in-part of application No. 09/326,177, filed on Jun. 4, 1999, now Pat. No. 6,434,567, which is a continuation-in-part of application No. 09/374,568, filed on Aug. 13, 1999, now Pat. No. 6,516,321, which is a continuation-in-part of application No. 09/130,934, filed on Aug. 7, 1998, now Pat. No. 6,345,268, which is a continuation-in-part of application No. 08/871,818, filed on Jun. 9, 1997, now Pat. No. 5,903,889, which is a continuation-in-part of application No. 08/727,293, filed on Oct. 9, 1996, now Pat. No. 5,895,461.

(60) Provisional application No. 60/023,126, filed on Jul. 30, 1996.

(51) Int. Cl.⁷ .............................................. G06F 17/30
(52) U.S. Cl. ........................... 707/104.1; 707/1; 705/1; 705/2; 705/3
(58) Field of Search ................................. 711/164, 163; 707/104.1; 712/226; 345/558; 714/12; 380/239; 709/231; 717/163; 705/1

(56) References Cited

U.S. PATENT DOCUMENTS 4,332,009 A * 5/1982 Gerson ........................ 711/164
4,384,288 A    5/1983 Walton
4,575,621 A    3/1986 Dreifus (List continued on next page.)

FOREIGN PATENT DOCUMENTS

| EP | 0234831 B1 * | 7/1989 | ........... G11B/27/02 |
| EP | 0323030 A2 * | 7/1989 | ........... G06F/11/10 |
| GB | 2154344 | 9/1985 | |
| WO | WO 01/33432 | 5/2001 | |
| WO | WO 01/35714 | 5/2001 | |

OTHER PUBLICATIONS

"Automatic Hypermedia Link Generation", IBM Technical Disclosure Bulletin, Jun. 1992, pp. 447–449.

"Glossary of Terms", attribution unknown, Jul. 18, 1999, pp. 1–6.

"Link Class Hierarchy Design", IBM Technical Disclosure Bulletin, vol. 34, No. 9, Feb. 1992, pp. 166–167.

(List continued on next page.)

Primary Examiner—Frantz Coby
(74) Attorney, Agent, or Firm—Quarles & Brady LLP

(57) ABSTRACT

A method to be used with a processor and at least a first record, the processor capable of facilitating at least a sub-set of possible record modifications including copying, moving, altering and deleting, the processor having access to characteristic sets which correspond to record codes, at least a first segment of the first record having characteristics that match a first characteristic set which distinguishes the first segment from other record segments, the first record also including a first record code which can be used by the processor and other processors to distinguish the first segment from other record segments, at least one processor performing at least one action based on the record codes in the first record, the method for verifying record codes prior to actions based thereon, the method comprising the step of, prior to allowing an action related to the first record code to be performed, verifying accuracy of the first record code.

40 Claims, 23 Drawing Sheets

U.S. PATENT DOCUMENTS

| | | |
|---|---|---|
| 4,817,050 A | 3/1989 | Komatsu et al. |
| 4,864,501 A | 9/1989 | Kucera et al. |
| 4,878,175 A | 10/1989 | Norden-Paul et al. |
| 4,887,212 A | 12/1989 | Zamora et al. |
| 4,893,270 A | 1/1990 | Beck et al. |
| 4,958,283 A | 9/1990 | Tawara et al. |
| 4,994,966 A | 2/1991 | Hutchins |
| 5,065,315 A | 11/1991 | Garcia |
| 5,146,439 A | 9/1992 | Jachmann et al. |
| 5,189,092 A | 2/1993 | Koslow |
| 5,204,947 A | 4/1993 | Bernstein et al. |
| 5,218,697 A | 6/1993 | Chung |
| 5,233,513 A | 8/1993 | Doyle |
| 5,253,362 A | 10/1993 | Nolan et al. |
| 5,283,884 A | 2/1994 | Menon et al. |
| 5,291,399 A | 3/1994 | Chaco |
| 5,297,249 A | 3/1994 | Bernstein et al. |
| 5,319,711 A | 6/1994 | Servi |
| 5,361,202 A | 11/1994 | Doue |
| 5,361,346 A | 11/1994 | Panesar et al. |
| 5,377,323 A | 12/1994 | Vasudevan |
| 5,392,386 A | 2/1995 | Chalas |
| 3,872,448 A | 3/1995 | Mitchell |
| 5,404,435 A | 4/1995 | Rosenbaum |
| 5,408,655 A | 4/1995 | Oren et al. |
| 5,418,942 A | 5/1995 | Krawchuk et al. |
| 5,434,974 A | 7/1995 | Loucks et al. |
| 5,438,655 A | 8/1995 | Richichi et al. |
| 5,459,860 A | 10/1995 | Burnett et al. |
| 5,490,250 A | 2/1996 | Reschke et al. |
| 5,506,984 A | 4/1996 | Miller |
| 5,515,534 A | 5/1996 | Chuah et al. |
| 5,530,852 A | 6/1996 | Meske, Jr. et al. |
| 5,535,372 A | 7/1996 | Benhase et al. |
| 5,541,583 A | 7/1996 | Mandelbaum |
| 5,558,638 A | 9/1996 | Evers et al. |
| 5,569,000 A | 10/1996 | Littecke et al. |
| 5,581,460 A | 12/1996 | Kotake et al. |
| 5,603,025 A | 2/1997 | Tabb et al. |
| 5,608,900 A | 3/1997 | Dockter et al. |
| 5,629,981 A | 5/1997 | Nerlikar |
| 5,646,416 A | 7/1997 | Van de Velde |
| 5,659,676 A | 8/1997 | Redpath |
| 5,708,825 A | 1/1998 | Sotomayor |
| 5,724,608 A | 3/1998 | Tohara |
| 5,740,252 A | 4/1998 | Minor et al. |
| 5,745,360 A | 4/1998 | Leone et al. |
| 5,745,908 A | 4/1998 | Anderson et al. |
| 5,754,857 A | 5/1998 | Gadol |
| 5,761,436 A | 6/1998 | Nielsen |
| 5,764,906 A | 6/1998 | Edelstein et al. |
| 5,781,900 A | 7/1998 | Shoji et al. |
| 5,790,856 A * | 8/1998 | Lillich .................. 717/163 |
| 5,794,050 A | 8/1998 | Dahlgren et al. |
| 5,806,079 A | 9/1998 | Rivette et al. |
| 5,815,830 A | 9/1998 | Anthony |
| 5,822,539 A | 10/1998 | van Hoff |
| 5,822,720 A | 10/1998 | Bookman et al. |
| 5,832,258 A * | 11/1998 | Kiuchi et al. ............... 712/226 |
| 5,833,599 A | 11/1998 | Schrier et al. |
| 5,842,224 A | 11/1998 | Fenner |
| 5,860,073 A | 1/1999 | Ferrel et al. |
| 5,860,136 A | 1/1999 | Fenner |
| 5,862,325 A | 1/1999 | Reed et al. |
| 5,867,562 A | 2/1999 | Scherer |
| 5,867,821 A | 2/1999 | Ballantyne et al. |
| 5,875,446 A | 2/1999 | Brown et al. |
| 5,878,421 A | 3/1999 | Ferrel et al. |
| 5,884,302 A | 3/1999 | Ho |
| 5,895,461 A | 4/1999 | de la Huerga et al. |
| 5,895,496 A * | 4/1999 | James et al. ................ 711/163 |
| 5,903,889 A | 5/1999 | de la Huerga et al. |
| 5,905,866 A | 5/1999 | Nakabayashi et al. |
| 5,905,991 A | 5/1999 | Reynolds |
| 5,940,843 A | 8/1999 | Zucknovich et al. |
| 5,942,986 A | 8/1999 | Shabot et al. |
| 5,963,205 A | 10/1999 | Sotomayor |
| 5,963,950 A | 10/1999 | Nielsen et al. |
| 5,970,505 A | 10/1999 | Ebrahim |
| 5,974,413 A | 10/1999 | Beauregard et al. |
| 5,987,475 A | 11/1999 | Murai |
| 6,014,677 A | 1/2000 | Hayashi et al. |
| 6,031,537 A | 2/2000 | Hugh |
| 6,038,573 A | 3/2000 | Parks |
| 6,094,649 A | 7/2000 | Bowen et al. |
| 6,128,635 A | 10/2000 | Ikeno |
| 6,141,663 A | 10/2000 | Hunkins et al. |
| 6,151,624 A | 11/2000 | Teare et al. |
| 6,157,914 A | 12/2000 | Seto et al. |
| 6,178,434 B1 | 1/2001 | Saitoh |
| 6,188,751 B1 | 2/2001 | Scherer |
| 6,208,998 B1 * | 3/2001 | Marcus .................... 707/104.1 |
| 6,230,283 B1 * | 5/2001 | Gambino .................... 714/12 |
| 6,272,505 B1 | 8/2001 | de la Huerga |
| 6,308,171 B1 | 10/2001 | de la Huerga |
| 6,345,268 B1 | 2/2002 | de la Huerga |
| 6,434,567 B1 | 8/2002 | de la Huerga |
| 6,507,837 B1 | 1/2003 | de la Huerga |
| 6,516,321 B1 | 2/2003 | de la Huerga |
| 2002/0083183 A1 * | 6/2002 | Pujare et al. ............... 709/231 |
| 2002/0159595 A1 * | 10/2002 | Boudreault et al. ......... 380/239 |
| 2003/0067472 A1 * | 4/2003 | Radke et al. ............... 345/558 |

OTHER PUBLICATIONS

"Multimedia Hyperlinks Automatically Created for Reference Documents", IBM Technical Disclosure Bulletin, PubNo=350, Jun. 1993.

Weibel, "Publish to Paper and the Web", Computing, vol. 9, Dec. 1996, p. 130.

"Text Formatting Rules", attribution and date unknown, c2.com/cgi/wiki?TextFormattingRules printed May 28, 2003, pp. 1–3.

"Turbo Pascal, Version 1.5 Demonstration", Microsoft evidence, 2003, pp. 1–4.

"U: Telecoms/Electronic mail/LANS", Current Awareness Abstracts, Oct. 1995, aslib.co.uk/caa/abstracts/open/95-1505.html, printed Apr. 10, 2003.

"User Generated Hypertext Links", IBM Technical Disclosure Bulletin, vol. 38, No. 10, Oct. 1993, pp. 453–454.

Z. Li et al, "Hypermedia Links and Information Retrieval", University of Southhampton, attribution and date unknown, pp. 1–11.

"What is Wiki", date unknown, http://wiki.org/wiki.cgi-?WhatIsWiki, p. 1.

"Wiki History", date unknown, last edited May 21, 2003, pp. 1–4.

"Wikipedia WikiWiki", date unknown, http://www.wiki.org, pp. 1–3.

A. F. Fountain et al, "MICROCOSM: An Open Model for Hypermedia with Dynamic Linking", Hypertext: Concepts, Systems, and Applications, Proceedings of the First European Conference on Hypertext, INRIA<France, Nov. 1990, pp. 289–311.

A. Salminen et al, "From Text to Hypertext by Indexing", ACM Transactions on Information Systems, vol. 13, No. 1, Jan. 1995, ACM 1046–8188/95/0100–0069 $3.50, c. 1995, pp. 69–99.

B. Goodman, "Web Documents Without HTML", Computer Shopper, Apr. 1997, p. 412.

B. J. Rhodes, et al, "Remembrance Agent: A Continuously Running Automated Information Retrieval System", Proceedings of the Frist International Conference on the Practical Application of Intelligent Agents and Multi–Agent Technology, Apr. 22–24, 1996, pp. 487–495.

B. Rhodes et al, "The Wearable Remembrance Agent: A System for Augmented Memory", The Proceedings of the First International Symposium on Wearable Computers (ISWC '97) Cambridge, MA, Oct. 1997 pp. 1–10.

C. Bailey et al, "An Agent–Based Approach to Adaptive Hypermedia Using a Link Service", Adaptive Hypermedia abnd Adaptive Web–Based Systems International Conference, AH 2000, Trento, Italy, Aug. 2000, http://eprints.ecs.soton.ac.uk/archive/00004465/02/ah2000.html.

C. H. Franke III, "Authoring a Hypertext UNIX Help System", Proceedings of ACM Conference on Computer Science, ACM 0–897971–767–5, c. 1995, pp. 238–245.

C. Keep et al, "Intermedia", The Electronic Labyrinth, copyright 1993–2000, pp. 1–2.

D. F. Brailsford, "Experience with the Use of Acrobat in the CVAJUN Publishing Project", ECHT '94 Proceedings, Sep. 1994 pp. 228–232.

D. Raymond et al, "Hypertext and the Oxford English Dictionary", Communications of the ACM, vol. 31m No. 7, Jul. 1988, pp. 871–879.

D. T. Change, "HieNet: A User–Centered Approach for Automatic Link Generation", Hypertext '93 Proceedings, Nov. 1993, pp. 145–158.

E. Wilson, "A Guide to Justus: An Overview of a Hypertext Legal Database", 5th BILETA Conference British and Irish Legal Technology Association, lileta.ac.uk/90papers/wilson.html, pp. 1–13, printed Apr. 11, 2003.

E. Wilson, "A Hypertext Interface for Automated Document Drafting", Law Technology Journal,vol. 1, No. 1, Oct. 1991, http://www.law.warwick.ac.uk/ltj/1–1e.html , pp. 1–14 printed May 29, 2003.

E. Wilson, "Cases for Justus" Preparing a Case Database for a Hypertext Information Retrieval System, Literary & Linguistic Computing, vol. 5, No. 1, 1990, Oxford University Press 1990, pp. 119–128.

E. Wilson, "Electronic Books: The Automatic Production of Hypertext Documents from Existing Printed Resources", attributed to Proceedings of the Fourth Annual Conference of the UW Centre for New Oxford English Dictionary, Information in Text, Waterloo, 1988, pp. 29–45.

E. Wilson, "Guiding Lawyers: Mapping Law into Hypertext", Artificial Intelligence Review 6, 1992, pp. 161–189.

E. Wilson, "Integrated Information Retrieval for Law Enforcement in a Hypertext Environment" ACM Portal—. Portal.acm.org/citation.cfm?id=62505&coll=ACM&dl= ACM&CF1D=11032774&CFTOKEN . . . , Jun. 25, 2003.

E. Wilson, "Integrated Information Retrieval for Law in a Hypertext Environment", Annual ACM Conference on Research and Development in Information Technology, 1988, pp. 663–677, ACM Portal, Portal.acm.org/citation.cfm?id=62505&coll=ACM&dl=ACM&CFID= 11032774&CFTOKEN . . . , Jun. 25, 2003.

E. Wilson, "Integrated Information Retrieval for Law in a Hypertext Environment", attributed to Proceedings of the SIGIR/ACM International Conference on Research and Development in Information Retrieval, 1988, ACM, 0–89791–274–B 88 06500 0663 $1.50, c 1988, pp. 663–677.

E. Wilson, "Links and Structures in Hypertext Databases for Law", Proceedings of the First European Conferences on Hypertext, INRIA, France, Nov. 1990, pp. 194–211.

E. Wilson, "Reference and Reference Inversion in Statutes and Cases: a Hypertext Solution", attributed to Informatics 10, 1989, CISTI Product Help 9919308 to 16173682126, printed Mar. 4, 2003.

G. Crane, "From the Old to the New: Integrating Hypertext into Traditional Scholarship", Hypertext '87 Papers, Nov. 1987, pp. 51–55.

G. Hill et al, "Applying Open Hypertext Principles t the ", University of Southhampton, attribution and date unknown, pp. 1–19.

G. Hill et al, "Extending the Microcosm Model to a Distributed Environment", ECHT '94 Proceedings, copyright 1994 ACM 0–89791–640–9/94/0009/$3.50, pp. 32–40.

G. Hill et al., "Microcosm and the: A Distributed Link Service", 1995/1996 Research Journal, University of Southhampton,, pp. 1–6.

G. Hill et al, "Open and Reconfiguarable Hypermedial Systems: A Filter–Based Model", CSTR 92–12, University of Southhampton, pp. 1–17.

G. Hill, et al, "Applying Open Hypertext Principles to the", attribution and date unknown, University of Southampton.

G. Krupka, "SRA: Description of the SRA System as Used for MUC–6", attributed to the Proceedings of MUC–6 Workshop, 1995, pp. 221–374.

G. Perlman, "Information Retrieval Techniques for Hypertext in the Semi–Structured Toolkit", Hypertext '93 Proceedings, Nov. 1997, pp. 260–267.

G. Salton et al, "Automated Analysis, Theme Generation, and Summarization of Machine–Readable Texts", Science, vol. 264, Jun. 3, 1994, pp. 1421–1426.

H. Davis et al, "A Framework for Delivering Large–Scale Hypermedia Learning Material", attribution and date unknown.

H. Davis et al, "Hypermedia and the Teaching of Computer Science: Evaluation an Open System.", attribution and date unknown, University of Southampton, pp. 1–8.

H. Davis et al, "Media Integration issues within Open Hypermedia Systems", attribution and date unknown.

H. Davis et al, "Microcosm: A Hypermedia Platform for the Delivery of Learning Materials", CSTR 93–10, University of Southampton pp. 1–11.

H. Davis et al, "Microcosm: An Open Hypermedia Environment for Information Integration.", CSTR 92–15, University of Southampton, pp. 1–18.

H. Davis et al, "Towards an Integrated Information Environment with Open Hypermedia Systems", ACM, Milano, Nov. 30–Dec. 4, 1996 p181–190.

H. J. Love, "Using Agent–Based Technology to Create a Cost Effective, Integrated, Multimedia View of the Electronic Medical Record", Symposium on Computer Applications in Medical Care, Oct. 28 to Nov. 1, 1996, New Orleans, pp. 441–444.

H. Kaindl et al, "Semiautomatic Generation of Dictionary Links in Hypertext", Submitted to DIS '95, Feb. 1, 1995, pp. 1–14.

J. Allen, "Automatic Hypertext Construction", PhD. Dissertation Cornell University, Jan. 1995.

J. Allen, "Automatic Hypertext Link Typing", ACM Proceedings for the Hypertext '96 Conference, Washington D.C., Mar. 1996, pp. 42–52.

J. Naughton, "Putting the Turbo in Pascal", Hardcopy, Jan. 1985, vol. 14, No. 1.

J. Robertson et al, The Hypermedia Authoring Research Toolkit (HART), Attributed to Proceedings of the European Conference on Hypertext, ACM 0–8791–640–9/94/0009/$3.50, Sep. 1994, pp. 177–185.

K. E. Willard et al, "W3 based Medial Information Systems vs Custom Client Server Applications", Univ_Minn_W#_Paper, http://archive.ncsa.uinc.edu/SDG/IT($/Proceedings/MedTrack/willard/UMHC_www/UMHC_www_paper . . . , date unknown, pp. 1–6 printed Jun. 4, 2003.

K. Osterbye et al, "The Flag Taxonomy of Open Hypermedia Systems", ACM Hypertext '95 Washington DC, 1996 ACM 0–89791–778–2/96/03 . . . $3.50, pp. 129–139.

K. W. Church et al, "Commercial Applications of Natural Language Processing", Communications of the ACM, v.38, n. 11, Nov. 1995, pp. 71–79 ISSN: 0001–0782, printed Mar. 13, 2003.

L. Carr, "The Microcosm Link Service and its Application to the World Wide Web", attribution and date unknown.

M. Bernstein, "An Apprentice That Discovers Hypertext Links", attribution and date unknown, pp. 212–223.

M. Bieber, "Issues in Modeling a "Dynamic" Hypertext Interface for Non–Hypertext Systems", Hypertext '91 Proceedings, Dec. 1991, pp. 203–217.

L. N. Garrett et al, "Intermedia: Issues, Strategies, and Tactics in the Design of a Hypermedia System", ACM CSCW, 1986, pp. 163–174.

Lotus, "Application Developer's Reference" Lotus Notes Release 3, copyright 1993, pp. 6–24 to 6–25.

Lotus, "Getting Started with Application Development", Lotus Notes Server for Windows Release 3, copyright 1993, pp. i. to 2–15.

L. N. Garrett et al, "Intermedia: Issues, Strategies, and Tactics in the Design of a Hypermedia Documents System", Proceedings of the 1986 ACM Conference on Computer-–supported Cooperative Work, 1986, pp. 163–174, ACM Portal, Portal.acm.org/citation.cfm?id=62505&coll=ACM&dl=ACM&CFID=11032774&CFTOKEN . . . , Jun. 25, 2003.

M. Bieber, "Providing Information Systems with Full Hypermedia Functionality", Working Paper Series Stern IS–92–29, Oct. 1992, pp. 2–13, printed May 16, 2003.

P. Lissack, "Concept Sampling—A New Twist For Content Analysis", attribution and date unknown, pp 1–40.

Microsoft Word 97 SR–2, demonstration pages, Microsoft exhibit, 2003.

N. Garrett, "Hypermedia: Issues, strategies, and Tactics in the Design of a Hypermedia System", ACM Portal Portal.acm.org/citation.cfm?id=637090&coll=ACM&di=ACM&CFID=11034774&CFTOKEN . . . ,Jun. 25, 2003.

P. Evans, "Speaking the Same Language", PC User, Issue 193, Sep. 22, 1992, pp. 57–58.

P. H. Lewis et al, "Content Based Retrieval and Navigation with Images in the Microcosm Model"University of Southampton, attribution and date unknown, pp. 1–5.

P. H. Lewis, et al, "Media–based Navigation with Generic Links", ACM Hypertext '96, Washington DC, pp. 215–223.

P. J. Brown, "A Help System Based o UNIX Manual Pages", date unknown, .dcs.ex.ac.uk/~brown/guide/spe.guide.help.html, printed Apr. 24, 2003.

P. J. Brown, "A Simple Mechanism for Authorship of Dynamic Documents", attribution and date unknown, pp. 34–42.

P. J. Brown, "Guide User Manual", Copyright 1985, Sixteenth Impression, Apr. 1995.

P. J. Brown, "Turning Ideas into Products: The Guide System", Hypertext '87 Papers, Nov. 1987, pp. 33–40.

P. J. Brown, "UNIX Guide: Lessons from Ten Years' Development", ACM Milano, Nov. 30 –Dec. 4, 1992, pp. 63–70.

P. Marshall, "Acrobat Common Ground Extend Reach Beyond Document Viewing", Info World Apr. 21, 1997, p. 105.

P. N. Smith, "Journal Publishing with Acrobat: the CAJUN Project", Electronic Publishing, vol. 6(4), Dec. 1993, 481–493.

P. Thistlewaite, "Automatic Construction and Management of Large Open Webs", Informatioln Processing & Management, vol. 33, No. 2, 1997, pp. 161–173.

P. Tyrvainen, "On Domain Modeling for Technical Documentation Retrieval", PhD Dissertation University of Technology (Espoo, Finland), Mar. 15, 1994, Published: Acta Polytechnica Scandinavica. 1994. pp. 1–163.

R. Hollom et al, "Integrating Internet Resource Discovery Services with Open Hypermedia Systems", CSTR 93–18, University of Southampton, pp. 1–18.

R. Wilkins et al, "A Direct Communication Model for Process management in an Open Hypermedia System", CSTR 93–14, University of Southampton, pp. 1–19.

Resource Workshop, Windows Programming Guide, Borland, c. 1991.

S. Ball, "New Approaches to Custom interfaces", Attributed to Proceedings of the AUUG 95, 1995, edu.au/special/conference/apwww95/papers95/sball/sball.html, pp. 1–11, printed May 5, 2003.

P. Thistlewaite et al, "Managing Large Hypermedia Information Bases: A Case Study Involving the Austrailian Parliament", Proceedings of AusWeb95 The First Australian World Wide Web Conference, Apr. 30 to May 2, 1995, pp. 223–227.

P. Thistlwaite, "Hypermedia in the Australian Parliament", . archive.org/web/19970129035318pastime.anu.edu.au/pbt/hypermedia.html, date unknown, pp. 1–8 printed Apr. 11, 2003.

S. Glinert, "A Pumped–Up Publishing Pro", Computer Shopper, Apr. 1997, pp. 462.

S. Goose et al, "An Architecture to Support an Open Distributed Hypermedia System", University of Southampton, 1995/1996 Research Journal, pp. 1–7.

S. Huffman et al, "Notes Explorer Entity–Based Retrieval in Shared, Semi–Structured Information Spaces", Proceedings of the ACM CIKM 96, Rockville MD, ACM 0–89791–873–8/96–11, c. 1996, pp. 99–106.

S. Matalon/S. Andrew, "Online Visits—Stump World Systems", attributed to /stumpworld.com/stump, Oct. 18, 1995.

S. Probets et al, "Dynamic Link Inclusion in Online PDF Journals", attribution and date unknown, pp. 1–14.

T. Joachims et al, "WebWatcher: A Tour for the World Wide Web", Proceedings of the International Joint Conference on Artificial Intelligence, 1997, citeseer.nj.nec.com/63787/16829. pp. 1–6 printed Jun. 4, 2003.

T. Starner er al, "Wearable Computing and Augumented Reality", M.I.T. Media Lab Vision and Modeling Group Technical Report No. 355, Nov. 1995, pp. 1–19.

Turbo Debugger for Windows, Resource Workshop User's Guide, Borland, c. 1991.

Turbo Pascal 1.5, Borland, c. 1992.

Turbo Pascal for Windows, Borland, c. 1998.

Turbo Pascal for Windows, Programmable Guide, Borland, c. 1987.
Turbo Pascal for Windows, Turbo Debugger for Windows, v. 3.1 User's Guide, Borland, c. 1988 & 1992.
Turbo Pascal for Windows, User's Guide, Borland, c. 1987. 1991.
Turbo Pascal for Windows, Windows Reference Guide, Borland, c. 1991.
V. Bush, "As We May Think", Atlantic Monthly, Jul. 1945, theatlantic.com/unbound/flashbks/computer/bushf.htm, pp. 1–19 printed Jun. 24, 2003.
W. Fitzgerald et al, "Using natural Language Processing to Construct Large–Scale Hypertext systems", submitted to the Eighth Knowledge Acquisition for Knowledge–Based Systems Workshop. Banff. Canada. Jan. 30 to Feb. 4, 1994.
W. Hall et al, "Linking the World Wide Web and Microcosm", attribution and date unknown, pp. 1–5, printed Jun. 4, 2003.
W. Hall et al, "Multimedia Teaching with Microcosm–HiDED: Viceroy Mountbatten and the Partition of India", attribution and date unknown, pp. 89–99.
W. Hall et al, "The Design and Implementation of an Open Hypermedia System", CSTR 92–19, University of Southampton, pp1–15.
W. Hall, "The History of the Microcosm Project", attribution and date unknown, Multimedia Research Group, pp. 1–6.
Understanding the Fabrikam Solution Architecture, Microsoft Corporation, Acey J. Bunch, Sep. 2001, 7 pages.
Creating Smart Tage In Web Parts, Microsoft Corporation, Chitsaz et al, Jul. 2001, 6 pages.
Adding Smart Tags To Web Pages, Microsoft Corporation, Paul Cornell, Jul. 2001, 5 pages.
Developing Simple Smart Tags, Microsoft Corporation, Paul Cornell, May 2001, 10 pages.
Developing Smart Tag DLLs, Microsoft Corporation, Paul Cornell, Apr. 2001, 15 pages.
What's New For "Office 11" Developers?, Microsoft Corporation, Paul Cornell, Dec. 2002, 21 pages.
Deploying Smart Tags With Enterprise Applications, John R. Durant, Jan. 2002, 10 pages.
Implementing Smart Tags With Enterprise Applications, John R. Durant, Jan. 2002, 6 pages.
Planning Smart Tags With Enterprise Applications, John R. Durant, Jan. 2002, 8 pages.
Automating The Testing Process For Smart Tag Development, Chris Kunicki, 2 pages (not dated).
Fabrikam Smart Tag Sample Setup Instructions, Chris Kunicki, Feb. 2002, 14 pages.
Microsoft Office & Visual Basics for Applications Developer, Interacting With Smart Tags, Microsoft Corporation, Chris Kunicki, 16 pages (not dated).
Integrating Office XP Smart Tags With The Microsoft.NET Platform, Microsoft Corporation, Powell, et al, Oct. 2001, 9 pages.
Exploring the Fabrikam 2.0 Solution Architecture, Microsoft Corporation, Frank C. Rice, Feb. 2002, 7 pages.
Building Smart Tags In Microsoft Visual Basic.NET, Microsoft Corporation, J. Sawyer, Oct. 2001, 22 pages.
Deployment of Managed COM Add–Ins In Office XP, Microsoft Corporation, Shineerson, et al, May 2002, 14 pages.
Accessibility In Office XP, 3 pages (not dated).
Complete Tasks Quickly With Smart Tags in Office XP, 5 pages (not dated).
Creating Your Own Smart Tags in Excel 2002, 8 pages (not dated).
How To Create A Smart Tag DLL In Visual Basic For Use In Office XP, 12 pages (not dated).
SmartTagActions Property, 19 pages (not dated).
Use MapPoint Smart Tags In Microsoft Word Or Excel, 3 pages (not dated).
What's New In Office XP Developer, Microsoft Office XP Developer, 5 pages (not dated).
Working with Smart tags, Microsoft Office XP Developer, 1 page (not dated).
SmartTag Enterprise Resource Kit, Microsoft Corporation, Jan. 2002.
msdn.microsoft.com/code/default.asp?url=.msdn–files/026/002/275/Sample%20Files/SmartTagRecognizer_cis.asp (8 pages) (not dated).
msdn.microsoft.com/code/default.asp?url=/msdn–files/026/002/285/Sample%20Files/Conversion_cis.asp (7 pages) (not dated).
Microsoft Corporation, Microsoft Word 97, screen printouts, pp. 1–4, 1997.
Glinert, A Pumped–Up Publishing Pro, Apr. 1997, Computer Shopper, p. 462.
Goodman, Web Documents Without HTML, Apr. 1997, Computer Shopper p. 412.
Marshall, Acrobat, Common Ground Extend Reach Beyond Document Viewing, InfoWorld, Apr. 21, 1997, p. 105.
Weibel, Publish To Paper And The Web, Dec. 1996, PC/Computing, p. 130.

* cited by examiner

MR1-1 Specification — 245, 246

| MR1-1 Column | MRRS1-1 Column | MR2 Spec. Column |
|---|---|---|
| MR1-1A | MRRS1-1A | MR2-1 Spec. |
| MR1-1B | MRRS1-1B | MR2-2 Spec |
| MR1-1C | MRRS1-1C | MR2-3 Spec. |
| ⋮ | ⋮ | ⋮ |

244 — MR1-1 Column
242 — MR1-1C
250, 240

Fig. 9

MR2-1 Specification — 250, 258, 260

| MR2-1 Column | MRRS2-1 Column | ARS2-1 Column |
|---|---|---|
| MR2-1A | MRRS2-1A | ARS2-1A |
| MR2-1B | MRRS2-1B | ARS2-1B |
| MR2-1C | MRRS2-1C | ARS2-1C |
| ⋮ | ⋮ | ⋮ |

256, 252, 254 — Resolution Rule Set

Fig. 10

DR/Address Look Up Table — 270, 274, 272

| DR | Address |
|---|---|
| "ECG Procedure" | Add-A |
| "X-ray Procedure" | Add-B |
| ⋮ | ⋮ |
| "Breast Cancer Bulletin" | Add-Q |
| "Colon Cancer Bulletin" | Add-R |
| ⋮ | ⋮ |

Fig. 11

XML Specification

| XML Type | XMLRS | XML Begin Tag | XML End Tag |
|---|---|---|---|
| Patient ID | XMLRS-1 | BT-1 | ET-1 |
| Heart Rate | XMLRS-2 | BT-2 | ET-2 |
| Image | XMLRS-3 | BT-3 | ET-3 |
| ⋮ | ⋮ | ⋮ | ⋮ |
| Abstract | XMLRS-Q | BT-Q | ET-Q |
| Diagnosis | XMLRS-Q+1 | BT-Q+1 | ET-Q+1 |
| Prescription | XMLRS-Q+2 | BT-Q+2 | ET-Q+2 |
| ⋮ | ⋮ | ⋮ | ⋮ |

Fig. 12

XML Specification

| XML Type | XMLRS | XML Begin Tag | XML End Tag |
|---|---|---|---|
| "Title" | XMLRS-1 | BT-1 | ET-1 |
| "Cross Reference" | XMLRS-2 | BT-2 | ET-2 |
| "Background" | ⋮ | ⋮ | ⋮ |
| "Summary" | ⋮ | ⋮ | ⋮ |
| "Brief Description of Drawings" | XMLRS-5 | BT-5 | ET-5 |
| - Fig. 1 | XMLRS-5-1 | BT-5-1 | ET-5-1 |
| - Fig. 2 | XMLRS-5-2 | BT-5-2 | ET-5-2 |
| - Fig. 3 | XMLRS-5-3 | BT-5-3 | ET-5-3 |
| ⋮ | ⋮ | ⋮ | ⋮ |
| "Claims" | XMLRS-7 | BT-7 | ET-7 |
| - Claim 1 | XMLRS-7-1 | BT-7-1 | ET-7-1 |
| - Claim 2 | XMLRS-7-2 | BT-7-2 | ET-7-2 |
| - Claim 3 | XMLRS-7-3 | BT-7-3 | ET-7-3 |
| ⋮ | ⋮ | ⋮ | ⋮ |

Fig. 16

XMLRS-5 (Corresponds to Description of Drawings)

Rule Set

- Search for segment:
    - After Summary end tag;
    - Before Detailed Description;
    - Natural Language search for:
        "Description of Drawings";
    - Must include at least one Figure of
        drawing description.

Fig. 17

XMLRS-7 (Corresponds to Claims)

Rule Set

- Search for segment:
    - Including "Claims" title;
    - After title, "1" must appear within 10
        terms followed by a single sentence
        ending in a period;
    - Search entire specification.

Fig. 18

XMLRS-5-1 (Corresponds to Figure 1 of Description of Drawings)

Rule Set

- Search for segment:
    - Which meets all XMLRS-5 requirements;
    - Which begins with "Fig. 1" and ends with a period or a semi-colon; and
    - Which is followed by a paragraph beginning with "Fig. 2" or a permutation thereof.

Fig. 19

XMLRS-5-1 (Corresponds to Claim 1 of the Claims)

Rule Set

- Search for a segment:
    - Which meets all XMLRS-7 requirements;
    - Begins with a "1" followed by a single sentence and ends with a period; and
    - Which is followed by a paragraph beginning with a "2".

Fig. 20

METHOD FOR VERIFYING RECORD CODE PRIOR TO AN ACTION BASED ON THE CODE

CROSS-REFERENCE TO RELATED APPLICATIONS

This application is a continuation-in-part of a U.S. patent application No. 09/374,568 which is titled "Method for Database Address Specification" which was filed on Aug. 13, 1999 by the present inventor and which issued as U.S. Pat. No. 6,516,321, which was a continuation-in-part of U.S. patent application Ser. No. 09/326,177 which is titled "Method for Specifying Enterprise-wide Database Address Formats" which was filed on Jun. 4, 1999 by the present inventor and which issued as U.S. Pat. No. 6,434,567, which was a continuation-in-part of U.S. patent application Ser. No. 09/247,349 which was filed on Feb. 10, 1999 and is entitled "Method and System for Automated Data Storage and Retrieval" which is a continuation-in-part of U.S. patent application Ser. No. 08/727,293 which was filed on Oct. 9, 1996 and is entitled "Method and System for Automated Data Storage and Retrieval With Uniform Address Scheme" which issued as U.S. Pat. No. 5,895,461, which in turn claims priority from provisional Application Ser. No. 60/023,126 which was filed on Jul. 30, 1996, and 09/247,349 filed May 3, 1999 also continuation-in-part of U.S. patent application Ser. No. 08/871,818 which was filed on Jun. 9, 1997 and is entitled "System and Method for Translating, Collecting and Archiving Patient Records" which issued as U.S. Pat. No. 5,903,889. This application is also a continuation-in-part of U.S. patent application Ser. No. 09/130,934 which was filed on Aug. 7, 1998 and is entitled "Method and System for Resolving Temporal Descriptions of Data Records in a Computer System" which issued as U.S. Pat. No. 6,345,268 which in turn was related to U.S. Pat. No. 5,903,889 referenced above.

STATEMENT REGARDING FEDERALLY SPONSORED RESEARCH OR DEVELOPMENT

Not applicable.

BACKGROUND OF THE INVENTION

The present invention relates to information processors and more particularly to a search system for generating links to a first information set which is referenced in a second information set and to a system which automatically inserts tags into records which can be used by other applications to identify specific types of information within the record.

The computer networking industry is constantly searching for new and improved ways to facilitate communication between network users and to access and manipulate data stored on network databases. To this end one common way to access data stored on a network has been to employ universal resource locators (URLs) common to the Internet. A URL is essentially an address which includes a plurality of fields which together operate as a pointer to information stored at a specific database address on a network. The address fields typically include two general information types including server specifier and specific data information. The server specifier information specifies a server which is linked to a database which includes specific information required. The specific data information provides a key which can be used by a server to determine the precise data required by a URL. For example, a first and typically broadest field for data stored on a hospital database may identify the hospital server (e.g., St. Mary's, Springfield, historical server). A narrower field may include specific data information indicating a specific hospital patient (e.g., a nine digit patient ID number).

When a URL is transmitted, the network routes the URL to the URL specified server. When the server receives the URL, the server parses the URL to identify the specific data information, retrieves the information and then performs some function (e.g., manipulation, providing the information back to the requesting network user, etc.) on the retrieved information.

One problem with URLs is that servers rely heavily on URL fields to identify URL specified data. As networks become more complex and as users and applications require access to relatively more specific data, additional fields are added to URLs and the URL scheme becomes much more complicated. For example, initially a hospital may include only a single server and therefore, once the hospital is specified in a single URL field, the server is known. However, as the hospital system expands and additional servers are added to the hospital system, additional server specifying fields need to be added. As another example, in a primitive system it may be sufficient to access complete ECG records for physician review. However, as a system becomes more complicated it may become desirable to enable access to more specific ECG record data such as heart rate.

Accessing specific data is further complicated when an application requires many small data segments from one or more records. For example, in a physician's report it may be advantageous to link references within the report to specific data stored at addresses linked to the report via the network. For instance, the desired links may be to an image, a heart rate and a diagnosis for a particular patient. In this case, three separate URLs would have to be specified by a user and linked to referencing text in the report, one URL for each of the image, heart rate and diagnosis. While such linking is advantageous, in many cases such linking is never contemplated because of the complexity of the required URL addressing scheme.

Recently another method and tool for accessing/manipulating data within a specific record has been developed which specifies universal "tags" which can be used within a record to earmark specific data types. An exemplary "tagging" language is the extensible markup language (XML). The tags are to be used by processor applications which are familiar with the tags to identify specific information types. Applications which are capable of recognizing tags are referred to hereinafter as "tag enabled" and records which include such tags are likewise referred to as tag enabled. Tags are typically paired including a "begin" tag and an "end" tag identifying the beginning and the end of a specific data type within a corresponding record. For example, in a patient record, a "<patient id>" tag may specify the beginning of a field including a patient ID and a corresponding "</patient id>" tag may specify the end of the patient ID field. Similarly, a "begin image" tag may specify the beginning of an image field while an "end image" tag specifies the end of the image field. Using a URL scheme a record can be retrieved by a tag enabled application. Thereafter, the application parses the record to identify specific data types required by the application and uses the identified data types.

Thus, tags and tag enabled applications can be combined with URLs to overcome some of the complexity associated with URL data specification within a specific record. Nevertheless, linking record segments and references together via URLs and tags requires knowledge about URL and operation and formats. For example, to link a reference in a first record to a segment in a second record, first the second record address has to be specified and the segment tags have to be specified. Then, the URL address of the second record and the tags of the record segment to be linked have to be linked to the reference in the first record. Because many record producers (e.g., physicians) do not have required URL and tag knowledge, despite the advantages associated with such linking, most such linking is foregone.

U.S. patent application Ser. No. 09/326,177 (hereinafter "the '177 reference") entitled "Method for Specifying Enterprise-Wide Database Address Format" which was filed by the present inventor on Jun. 4, 1999 describes a system whereby URLs are automatically generated for data within a record thereby streamlining the process of linking references in one record to data stored at other network locations. To this end information in a first record is searched for data references (DRs) which reference other records. When a DR is identified, other record information is sought for constructing a URL address to the record associated with the data reference. After a URL corresponding to the record associated with the data reference is constructed, a link to the referenced record is formed. Exemplary links include hyperlinks, importation of the referenced record information into the referencing first record or electronic document, etc. Both real time and batch processing are contemplated.

A wrinkle of complexity is added to the referencing scheme whereby modifier references (MRs) may be used to further specify a specific record or record segment when a DR is identified. In this case, when a DR is identified, the record is further examined to identify modifier references (MRs) which identify a specific segment of a record which is associated with the data reference. When an MR is located, additional information is sought within the record for building an address to the record or record segment referenced by the DR/MR combination. Once again, a link is created between the referencing record and the referenced record or record segment.

Unfortunately, the '177 reference system also has several shortcomings in the area of html linking. The '177 reference recognizes that various search rules can be employed by a processor assigned the task of constructing referenced record addresses. Nevertheless, in the interest of simplifying explanation of the novel concepts in the '177 reference, the '177 reference assumes a simple searching rule wherein only the term immediately preceding a DR is examined to locate an MR. For example, where an ECG DR is located, only the term preceding the ECG term is sought for MRs (e.g., admission, post-op, etc.).

While such a simple MR search rule is advantageous for explanation purposes, it has been recognized that such a simple rule is most likely inadequate for most practical automatic linking systems for a number of reasons. First, such a simple rule would likely fail to identify many intended links. For instance, while many physicians may enter the phrase "post-op ECG" into a report, other physicians may enter the phrase "post-op exemplary ECG" to refer to a similar record. In this case, the intermediate term "exemplary" would render the phrase "post-op exemplary ECG" unrecognizable as a DR/MR combination. In fact, in this regard, an MR and a corresponding DR may be separated by several (e.g., 10) terms or an MR may follow a DR.

Second, even where a rule is adopted which accommodates terms between an MR and a DR, there may be instances where two DRs fit the required relationship with respect to a single MR or where two MRs fit the required relationship with respect to a single DR. For example, the phrase "post-op ECG and admission report" may be included in a record. In this case, a rule which specifies that an MR may be within five terms of a DR would be confusing as the exemplary phrase could reference a post-op ECG or an admission ECG or both.

Third, it has been recognized that in the case of certain advantageous linking features, simple address constructing rules may cause additional confusion. For example, it would be advantageous to have a system which supports more than a single MR level. For instance, where "ECG" is an exemplary DR, a first level MR (i.e., MR1) may be "post-op", indicating a post-operation ECG and a second level MR (e.g., MR2) may be "heartbeat waveform". While entering a report, a physician may reference a "post-op ECG heartbeat waveform" corresponding to a specific segment of a post-op ECG report which includes a heartbeat waveform. In this case, the system may support links to an entire ECG report (for example, the most recent ECG report), an entire post-op ECG report (independent of whether or not the post-op ECG report is the most recent report), a graph corresponding to the post-op ECG heartbeat waveform, a graph corresponding to a most recent ECG heartbeat waveform, or to any combination of an ECG report, a post-op ECG report, the post-op ECG heartbeat waveform or the most recent ECG heartbeat waveform. Unfortunately, there is no way for a processor to determine which of several links should be formed using a simple rule such as checking the term prior to a DR to identify an MR.

Generally there are two different types of automatic hyperlink generating systems including systems that generate hyperlinks effectively in real time (i.e., as text is being entered) and systems that generate hyperlinks in batch form. Real time systems are advantageous in that links are updated routinely as text is entered into a document or as document text is altered and hence links are always current. Thus, a link can be used almost immediately after text (e.g., a DR) associated with the link is entered by a system user. One problem with real time systems, however, is that system users are often distracted when text changes appearance during a linking action to earmark the text as a hyperlinked phrase. For instance, some systems may change black text to blue text to identify a link when a link is to be made.

Batch type hyperlink generating systems, as the label implies, receive a text segment or, in some cases, may receive an entire document, and search the entire text segment or document to identify suitable DRs and/or DR/MR combinations to be hyperlinked to other documents. Thus, for instance, after a batch system user uses a word processor to create a document, the document is submitted to the batch hyperlinking system which may identify fifty separate hyperlinkable phrases within the document text and thereafter generates fifty hyperlinks within the document to fifty other documents. Batch type linking systems have proven to be far less distracting to use than real time systems.

Unfortunately, with batch type systems, under certain circumstances inadvertent, incorrect and undesirable linking may occur. For instance, after a document is initially created and links are added to the document via a batch linking operation, when the document is altered, the links in the document may no longer be correct. For instance, where the phrase "Mike Johnson's CT heart image" in a document is linked to a CT heart image for Mike Johnson and a physician edits the document so that the phrase reads "John Thomas' CT heart image", the edited phrase most likely should no longer be linked to Mike Johnson's CT heart image. Instead, where a CT heart image for John Thomas' exists, it may be appropriate for a new link to be made to the John Thomas image. Similarly, where a system stores both a general pamphlet related to CT imaging and Mike Johnson's CT heat image, an initial document phrase "CT heart image" may properly be linked via batch processing to the general CT imaging pamphlet. However, when a post-batch processing document edit adds the qualifier "Mike Johnson's" before the initial phrase "CT heart image", despite the fact that the appropriate link may be to Mike Johnson's CT heart image, the initial link will still exist to the CT imaging pamphlet—an undesired and inappropriate link.

Incorrect links lead to system user confusion and, in the case of health records, may lead to unacceptable misdiagnosis of physical ailments. For instance, where a physician links to one patient's CT heart image believing that the physician is linking to another patient's CT heart image, the consequences may be devastating.

Similarly unacceptable results can occur when the document or record is analyzed by a batch type processing system for document or record characteristics that are used to identify markup language tags (e.g., XML tags) or other record codes to be inserted into the document, the tags or codes are inserted and then the record is subsequently modified. For instance, a batch process may add XML tags around the text "Hillary Clinton" which is later changes to "the town of Clinton, Ill.". In this case XML tags corresponding to Hillary Clinton but remaining associated with the town of Clinton would clearly be erroneous and may be employed subsequently to cause unintended and incorrect linking or other actions.

Therefore, it would be advantageous to have a method and apparatus which facilitates unambiguous linking between record references in a first record and referenced records or segments in a second record. In addition, it would be advantageous to have a method and apparatus for automatically inserting markup language tags such as XML or HTML into records either as the records are formed or in a batch mode. Furthermore, it would be advantageous to have a batch link generating system where document edits that follow batch linking do not result in erroneous hyperlinking and other tag or code related actions.

BRIEF SUMMARY OF THE INVENTION

Hereinafter the term "specifying reference" (SR) will be used to refer generically to each of a DR and a DR/MR combination or a DR/MR/MR combination.

An exemplary embodiment of the invention includes a system wherein link ambiguity is rendered unambiguous by imposing a rule set which specifies which of two or more SRs should be selected when two or more SRs and overlap. It has been recognized that in most cases when two possible DR/MR combinations or DRs, which overlap are identified, the user wishes to form a link to a record segment associated with the longer of the two SRs as the longer of the SRs typically more specific than the shorter. Therefore, a preferred rule is that the longest of two SRs is selected. For example, when a first DR/MR combination is "previous ECG" and a second DR/MR combination is "previous ECG report", a link is formed to the combination "previous ECG report" as that reference is the longest and most specific.

The invention also includes a system wherein link ambiguity between DRs or MRs which are associated with more than one other DR or MR is rendered unambiguous through specification of rules used to select one DR/MR combination over another. For example, where the term "previous" is proximate both DRs "ECG" and "X-ray" such that the term previous could modify either of the two DRs, a rule set is specified which enables the system to select one DR/MR combination over the other. For instance, the rule set may specify that when a single MR is proximate two DRs, the system selects the DR/MR combination corresponding to the first DR or corresponding to the DR which is closest to the MR. Other rule sets, are contemplated, the important characteristic of the sets being that some rule set is provided to minimize ambiguity.

In addition, the invention also includes a system wherein, instead of building URLs when an SR is identified, a processor uses a lookup table to identify a suitable URL which corresponds to the identified SR. For example, in the case of a medical facility, medication information and dosing regimen may routinely be referenced in patient records. In this case, where each brochure and schedule is electronically stored at a known address and can be referenced by a specific SR, the SRs and known addresses are correlated and stored in a lookup table. When an SR is recognized in a record, the table is accessed, the address corresponding to the SR is identified and a link is formed. This aspect of the present invention is particularly useful where a small number of records may routinely be referenced in other records.

Moreover, the invention also includes a system which automatically inserts tags into records to render the records useful in tag enabled applications. To this end, it has been recognized that record segments which are often related to specific types of data will have a specific and recognizable format or will include specific text or graphical indicia. Because the formats, text and/or indicia are recognizable, the information in the formats can be identified as a specific type by a processor which is programmed to search for and identify such information. Once a segment type is known, tags which can be recognized by a tag enabled application can be inserted in the record which is then tag enabled (i.e. can be used by the tag enabled application).

Thus, one object of the present invention is to eliminate ambiguity between SRs where two SRs overlap or a shorter SR is included within a longer SR.

Another object of the invention is to automatically determine whether or not tags may suitably be added to a record to identify specific record segments and information types therein and, when appropriate, to automatically add the tags to render the record tag enabled so that a tag enabled application can identify specific information within the record.

One other object of the invention is to ensure that, when modifications are made to a record which includes tags, the tags remain correct. To this end, the invention includes a feature whereby a processor monitors modifications to a record which includes tags and, when a modification effects tag correctness, the processor performs one of several different functions to ensure that incorrect tags are removed from the record. To this end, one function may be to eliminate all tags in the record. An extended function may be to, after eliminating all tags, reinsert tags into the record where appropriate. Other functions are contemplated.

One other object of the invention is to facilitate a simpler linking process for linking references to a first record which appear in a second record to the first record. To this end, a look-up table is used.

A further object of the invention is to ensure that tags are verified prior to being used to facilitate any action. In this regard, it has been recognized that under certain circumstances tags or record codes that have been added to a record or document in the past may in fact be rendered inaccurate by subsequent changes to the record or document or, indeed, to records that are linked to a document. For example, where a batch linking process is performed on a record and the record is stored, a system user may subsequently access and alter the record content in a manner that renders at least some of the record tags inaccurate.

To overcome the problems associated with inaccurate tags and codes, the invention verifies that tags and/or codes are accurate prior to any action related thereto being performed. For instance, verification may include, when a command requiring an action related to a tag is received, first verifying that the tag is accurate. As another instance, verification may be performed whenever an editing cursor is removed from a document segment that is associated with a specific tag or record code. Similarly, where a sub-set of record segments include information that can be used to characterize a first record segment for tagging or coding purposes, verification may occur whenever an editing cursor is removed from the related segment sub-set. As one other instance, whenever a record is stored or accessed tags may be re-verified. Here, verification upon access ensures that if a DR or DR/MR combination is no longer valid, tags associated therewith will be removed from an accessing document. Other methods to ensure tag verification prior to an action include re-identifying tags and codes in a record or record sections prior to e-mailing, when the record or segment is copied into an operating system clipboard (assuming it may be pasted or inserted into another record by a program presumably unable to verify tags), or when the modified record or record portion is inserted into another record.

Verification may take several different forms including, but not limited to, eliminating tags, rendering tags unactionable until a user recognizes that the tags may not be accurate and requiring affirmative recognition of potential inaccuracy by the system user, eliminating tags and then re-identifying tags and codes, etc. In addition, tag verification may be on a document wide basis so that all tags are verified whenever any document modification is made or, in the alternative, may be on a document section basis whenever a modification is made to a document segment or segments that are known to only affect the characteristics of a sub-section of the document.

In some embodiments tags placed in a record by the user can be left in the record and need not be removed prior to an action being performed. In other cases user defined tags and codes may have to be removed for automatically inserted (e.g., batch inserted) tags and codes to be valid. For example, when the automatically inserted tags are XML tags and the user provides additional XML tags that incorrectly span a series of the automatically inserted tags that are in a fixed cascading or nested hierarchy, the user defined tags may have to be eliminated. Here, the user may be given a choice as to whether to accept the automatically provided tags and the removal of the user provided tags or to reject the automatically provided tags. The step of requesting the guidance of a user may be used any time a user provided tag is in conflict with tags that are automatically provided.

It should be appreciated that the batch verification aspect of the present invention is provided for the same reason as the real time code verification aspects described below. Both batch and real time verification prior to performance of an action associated with a record code are provided to ensure that codes are accurate and hence to avoid confusion.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF THE SEVERAL VIEWS OF THE DRAWINGS

FIG. 9 is a schematic diagram illustrating another MR specification according to the present invention;

FIG. 10 is a schematic diagram of our exemplary second level MR specification according to the present invention;

FIG. 11 is a schematic diagram of an exemplary DR look-up table according to the present invention;

FIG. 12 is schematic diagram of an exemplary XML specification according to the present invention;

FIG. 16 is a schematic diagram of another XML specification according to the present invention;

FIG. 17 is detailed schematic diagram illustrating an exemplary XMLRS of FIG. 16;

FIG. 18 is similar to FIG. 17, albeit illustrating another XMLRS of FIG. 16;

FIG. 19 is a schematic illustrating a nested XMLRS of FIG. 16;

FIG. 20 is similar to FIG. 19, albeit illustrating a second nested XMLRS of FIG. 16;

FIG. 27a is a schematic diagram illustrating a description box according to the present invention while

DETAILED DESCRIPTION OF THE INVENTION

Although the present invention is meant to be used in a plurality of different environments, in order to simplify this explanation, unless indicated otherwise, the invention will be described in the context of a medical facility named "St. Mary's, Springfield". In addition, while the present invention is described in the context of a word processor, the present invention is meant to be used in conjunction with other data manipulation programs such as database management programs, spread sheet programs, etc. Moreover, while some of the examples hereinafter are presented in the context of real time processing and others are presented in the context of batch processing, each real time example could be performed in batch and vice versa.

Furthermore, while other "tagging" languages are contemplated and may be used with the present invention, the invention will be described herein in the context of XML and XML tags. Nevertheless, it should be understood that the invention is not to be so limited.

Throughout this specification the phrase "natural language processing" is used to describe one type of search capability in various contexts. Natural language processing is well known in the word processing art and has been described in some detail in a several previously issued U.S. patents including U.S. Pat. Nos. 4,887,212, 4,994,966, 5,884,302 and 5,794,050, each of which are incorporated herein by reference for the purpose of generally teaching the concepts which together comprise natural language processing. Generally, natural language processing constitutes a system whereby a processor can use rules which are generally acceptable within a language to determine the meaning of a string of words. For example, the processor is typically equipped to recognize words and phrases as prepositional phrases, nouns, verbs, adjectives and also can identify relationships between proximate words and phrases. For instance, if the exemplary phrase "ECG report and x-ray image" were considered, the processor could recognize that the term "ECG" modifies the term "report" while the term "x-ray" modifies the term "image." The patents referenced above should be relied on for additional teachings in this regard.

Figure 1:
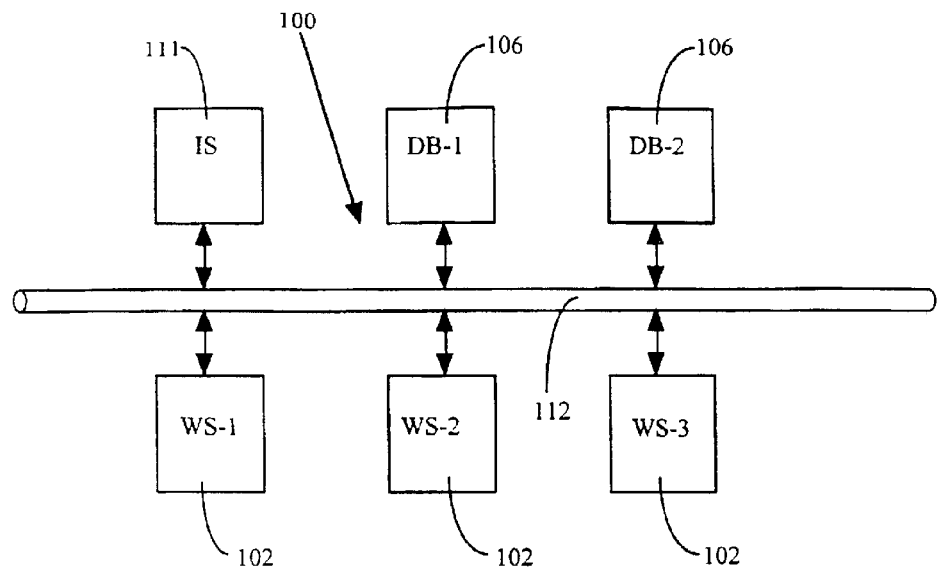
FIG. 1 is a schematic diagram of a computer network used with the present invention.

Referring now to the drawings wherein like reference characters and numbers represent like components, data constructs and signals throughout the several views and, specifically, referring to FIG. 1, the invention is illustrated as a computer network 100 including a plurality of workstations 102 which may be personal computers, hand held devices, etc., and a plurality of databases 106. Network 100 also includes an Information System (IS) 111. Databases 106, system 111 and workstations 102 may communicate with each other via a communication network 112 which may be a combination of local and wide area networks using Ethernet, serial line, wireless, or other communication standards. Network 112 may also be arranged so as to be part of the Internet or as an individual Intranet.

Figure 2:
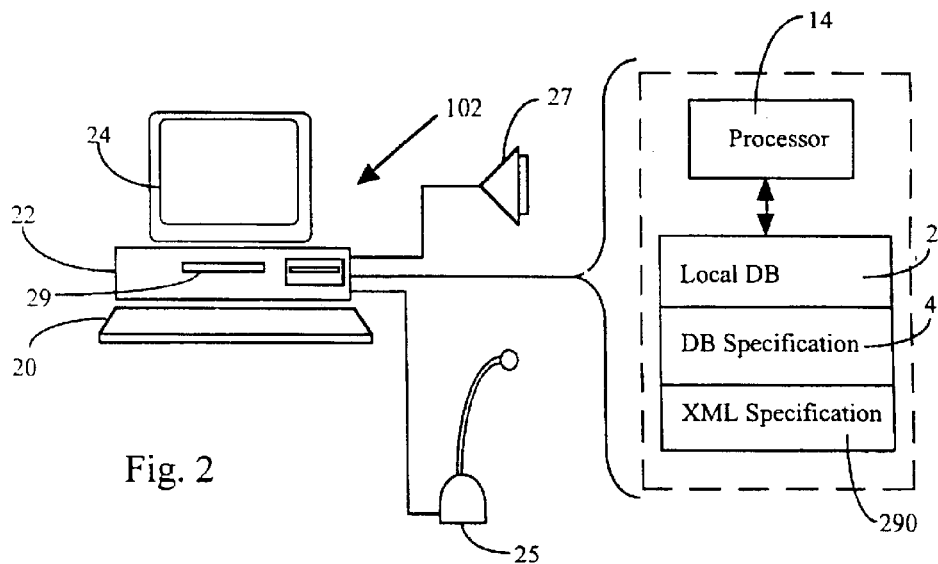
FIG. 2 is a schematic diagram of a work station of FIG. 1.

Referring to FIG. 2, each workstation 102 includes user interface hardware including a keyboard 20, a computer 22 and a video display 24. In addition, as illustrated, the hardware may also include other data input devices such as a microphone 25 supported by voice recognition software (not illustrated), a wireless data link 27 for receiving data from a remote information collection device (not illustrated), a disk drive 29 linked to computer 22 to receive data via a disc or the like, or any other data receiving devices. Computer 22 includes a processor 14 which is linked to a local DB2 and supports a network browser or similar display, entry and retrieval program.

Word processor 14 runs under the direction of computer 22 and performs all of the functions (e.g., creation of documents, modification of documents, storage and retrieval, etc.) which are typically associated with a conventional word processor. In addition, processor 14 is also capable of additional functions including recognition of data references (DRs) in data records, identification of hypertext links between the DRs and data records, recognition of XML information segments within records and insertion of XML tags to render records tag enabled. Various characteristics of word processor 14 which facilitate these features are described separately below.

1. Creating Unambiguous Record Links

A U.S. patent application Ser. No. 09/326,177 entitled "Method for Specifying Enterprise-Wide Database Formats" (hereinafter "the '177 reference") which was filed on Jun. 4, 1999 by the present inventor teaches, among other things, a system wherein a word processor can form links between references to a record and the referenced record when the references appear in a second record. The '177 reference specification is incorporated herein by reference. Nevertheless, some characteristics of the system described in the '177 reference which are particularly pertinent to the present invention are repeated here in the interest of clarity.

Referring still to FIG. 2, local DB 2 includes DR specification 4 which is accessible and useable by processor 14 to create links between references to a first record and the first record when the references appear in a second record. To this end, referring also to FIG. 3, specification 4 includes both a DR table 5 and a DR resolution rule set (RRS) 7. Table 5 includes two columns including a DR column 30 and an address rule set (ARS) column 32. DR column 30 includes a list of DRs. A DR is a unique phrase or word which may be used in a record to refer to another record or record segment. In the context of a medical facility an exemplary DR may be as simple as "medication given", "ECG report", or "Admission NMR heartbeat". As explained in more detail below, when a processor linking feature is selected, processor 14 searches for DRs in a specified record and, when a DR is identified, links the DR to a record or record segment associated with the DR via a hyperlink or other mechanism. In the preferred embodiment of the invention the longest DRs in a DR list include more than one word.

ARS column 32 includes a separate ARS for each DR in column 30. Exemplary ARS-1 is identified by numeral 44. In one embodiment which includes relatively complex ARSs each ARS includes a plurality of related data constructs which together define an address format for the corresponding DR in column 30, define rules for identifying information for forming an address having the address format and define rules for using the identified information to form an address. To this end, referring to FIG. 4, exemplary ARS 44 specifies an address format including six address fields 56, 58, 60, 62, 64 and 66.

For each field, ARS 44 specifies that the field is either "fixed" or "variable". Fixed means that the text (i.e. data object) used to instantiate a field is always the same. For example, for St. Mary's of Springfield, it will be assumed that all DBs are identified generally by a universal resource locator (URL) segment "http://hww.st_mary.springfield". In this case, all DRs include a first fixed field 56 wherein the text to instantiate the field comprises: http://hww.st_mary.springfield". As another example, each time a medication is given to a patient, an administration record is required. In this case, an exemplary fixed text field specifying the occurrence of medication administration is "medication/given".

Figure 4:
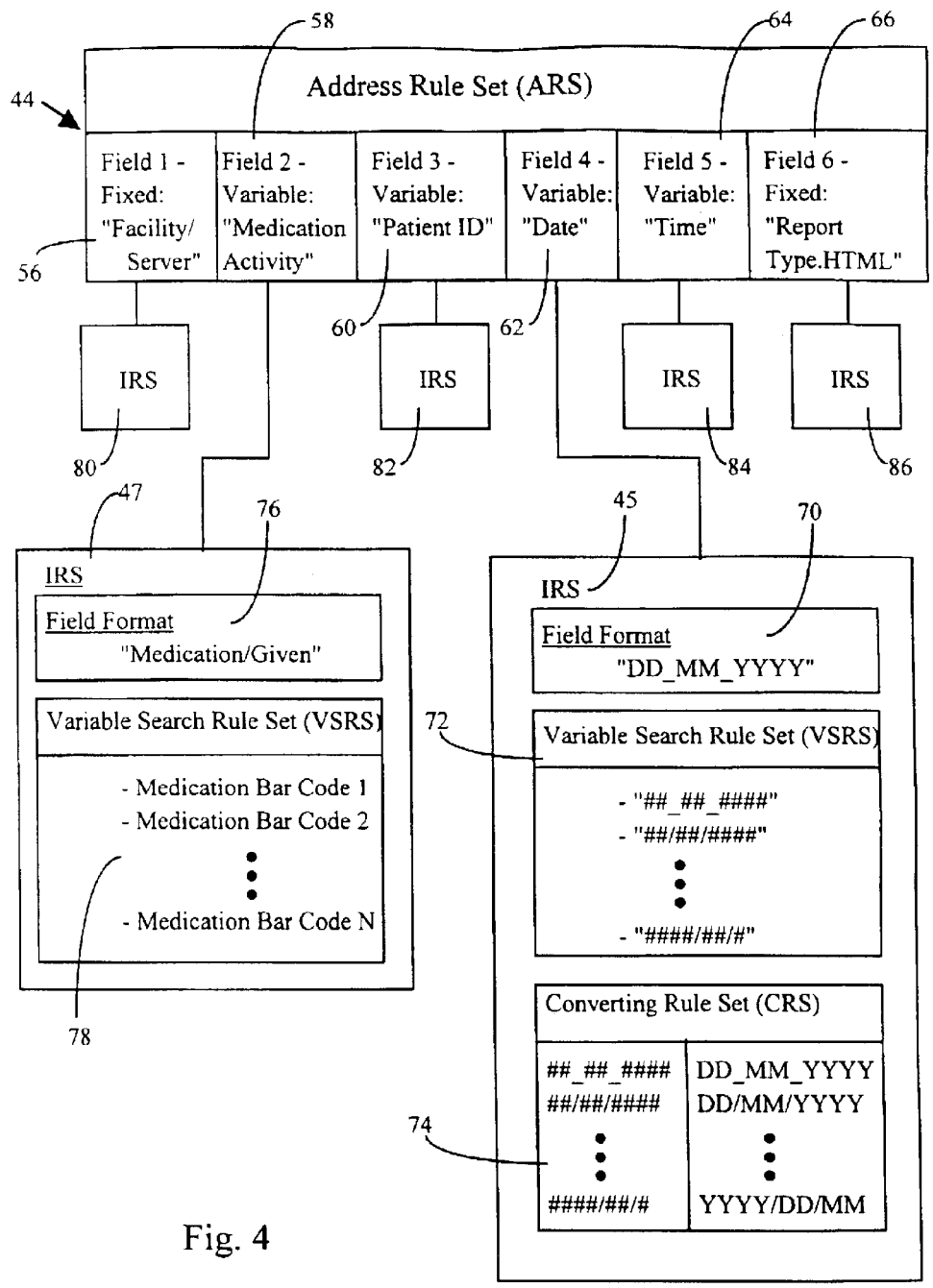
FIG. 4 is a schematic diagram of an exemplary ARS of FIG. 3.

Referring still to FIG. 4, variable means that text used to fill or instantiate a field may vary from record address to record address. For example, the character string used to fill a date field will vary daily, the character string used to fill a time field will vary as time lapses and the character string used to fill a patient field will vary depending on which patient a record is associated with. In FIG. 4, fields 56, 58 and 66 are fixed while fields 60, 62 and 64 are variable.

In addition to specifying fixed and variable characteristics, ARS 44 also specifies a field name for each field. For example, for fixed fields 56, 58 and 66 ARS 44 specifies "facility/server", "medication/given" and "report.html". For variable field 60, ARS 44 specifies name "patient ID", for field 62 ARS 44 specifies name "Date" and for field 64 ARS 44 specifies name "Time". These field names are not required by processor 14 but rather are provided to help a system user define data type definitions and to visualize address and record formats. To this end, the field names should generally describe the type of information corresponding to the field. Hence the name "Date" corresponds to the date field and so on.

For each field 56–66, ARS 44 also provides a field instantiation rule set (IRS). As the characteristics of each IRS are similar, only IRSs 45 and 47 corresponding to fields 62 and 58, respectively, are illustrated and described in detail. IRS 45 includes a field format 70, a variable search rule set (VSRs) 72 and a conversion rule set (CRS) 74. Similarly, IRS 47 includes a field format 76 and a variable search rule set (VSRs) 78.

For fixed field 58, field format 76 constitutes the specific fixed text to be placed in the field. For example, for field 58, the field format includes "medication/given". VSRs 78 includes a rule set which provides rules which indicate how, based on a set of information, to determine that medication has been given. For example, rules to determine if a medication has been given in the present example include a list of every possible medication bar code used at the St. Mary's facility. When one of the listed bar codes is identified in a set of information, medication administration is assumed. Although not illustrated, VSRs 78 may include other rules for determining if a medication has been administered. Although the rule sets described herein are relatively simple, other more complex rules are contemplated.

Referring still to FIG. 4, field format 70 constitutes a variable character string specifying an information format required to instantiate field 62 with a date. In the present example, the variable character string is "DD_MM_YYYY" where DD indicates the day of a month, MM indicates a number corresponding to the month of a year (i.e. "05" is May) and YYYY indicates a four digit year (e.g. 1996). Thus, independent of how a date appears in an information set, the date must be provided in the specified variable character string form "DD_MM_YYYY" according to format 70

VSRs 72 includes a rule set which is used to search an information set for any date specifying information which can be used to instantiate variable field 62. To this end, VSRs 72 specifies a separate rule corresponding to each possible format in which a date might appear in an information set (see exemplary rules in VSRs 72). Exemplary rules include "##/##/####", "##_##_##" and "####$_{13}$ ##$_{13}$ ##" where each "#" corresponds to a number in the character string. Many other rules are contemplated including rules which account for spelled out months, other date patterns and so on.

Referring still to FIG. 4, with respect to variable field 62, while corresponding date specifying information may appear in a record or information set in any of several different formats, as indicated by format field 70, ARS 44 requires a specific format for instantiating variable field 62. Thus, conversion rules for converting date information to specific format 70 are required. To this end, CRS 74 includes conversion rules corresponding to field 62. In FIG. 4, an exemplary rule correlates "##/##/####" with "DD/MM/YYYY" meaning the first two "#'s" are assumed to correspond to "DD", the third and fourth "#'s" are assumed to correspond to "MM" and the last four "#'s" are assumed to correspond to "YYYY". Thus, if a string having the form "##/##/####" is located, format "DD/MM/YYYY" is assigned to corresponding numbers. Then, D's, M's and Y's in format "DD/MM/YYYY" can be mapped to D's, M's and Y's in field format 70 (i.e. into "DD_MM_YYYY") to make a data conversion and provide information to instantiate field 62 with a date having format 70. Similar IRSs (e.g. 80, 82, 84, 86) are provided for each of fields 56 through 66.

Referring again to FIGS. 2 and 3, assuming a complete DR specification 4 is stored on DB 2, a first record which includes at least some of the DRs in table 5 is currently accessed by processor 14 and that the record linking function of processor 14 has been selected. In this case, processor 14 searches the first record for DRs which appear in column 30. When a DR is identified, processor 14 accesses table 5 and identifies the ARS which corresponds to the identified DR. Thereafter, processor 14 uses the ARS to identify information required to construct an address for the record or record segment associated with the identified DR and the format of the information, gleans the required information from the first record (or from some other source, e.g., may request some information or retrieve information from other network 100 components), constructs an address identifying the referenced record and links the address to the identified DR.

Linking may include modifying the appearance of the identified DR and linking such that when the DR is selected (e.g., via a mouse controlled cursor), processor 14 uses the address to retrieve the referenced record and display the record for observation. Other linking characteristics are contemplated.

It has been recognized that some systems may support both long and short DRs wherein a long DR constitutes a short DR and some additional text. For example, one short DR may include the term "ECG" while a relatively longer DR includes the phrase "previous ECG". In this case, a system which operates as described above would likely result in some confusion. For instance, in this case the system would likely provide two separate links to the term "ECG", one link to an "ECG" document and another link to a "previous ECG" document.

According to the present invention, instead of allowing such ambiguity, an inventive rule set is imposed on the system whereby, when two or more DRs are identified within a record and one or more of the identified DRs is encompassed in a longer DR, the longer of the DRs is selected for forming an address and creating a link. Thus, in the present example where DRs "ECG" and "previous ECG" are both identified, processor 14 selects "previous ECG" for addressing and linking purposes.

Figure 3:
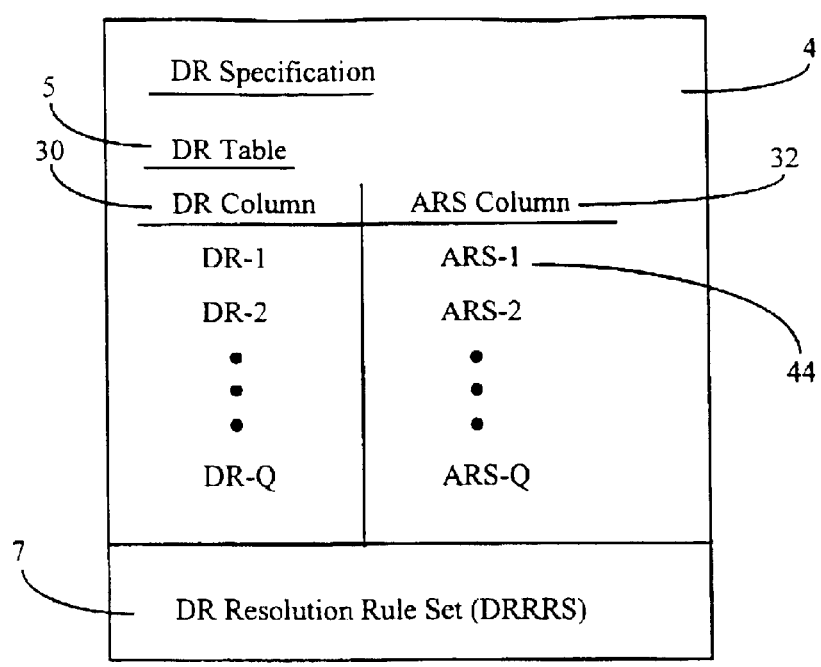
FIG. 3 is a schematic diagram of a DR specification according to the present invention.

To this end, referring still to FIGS. 2 and 3, DR RRS 7 specifies rules which facilitate selection of the longest of two DRs when one DR consists of another DR and additional text. Although the present invention includes preferred rules for carrying out the function of identifying the longest DR, in the broadest context of the invention, the manner in which RRS 7 performs this function is irrelevant. Nevertheless, this function should be performed efficiently. For example, in one system the longest possible DR may constitute a phrase including five terms. In this case, when a DR is recognized, prior to forming an address for the record corresponding thereto, processor 14 should check the five terms thereafter to ensure that the identified DR is not part of a longer DR. Where the identified DR is not a part of the longer DR the processor can form the address. However, where the identified DR is part of a longer DR, the processor should proceed to form an address corresponding to the longer of the two DRs.

According to one efficient search technique, DRs may be stored in an alphabetical table wherein, as terms and phrases are recognized as being parts of DRs, processor 14 begins with the longest possible DR corresponding to a phrase or text and moves on to shorter phrases or text only as additional terms or letters are considered. For instance, where three DRs are "ECG report heart rate", "ECG report" and "ECG", during data entry and real time processing, when the term "ECG" is entered, processor 14 initially assumes the longest DR "ECG report heart rate". Thereafter, assuming data entry next provides the term "report", processor continues to assume longest DR "ECG report heart rate". However, if the next term entered is "taken", processor 14 recognizes that longest DR "ECG report heart rate" is no longer valid and must search the alphabetical DR listing for the next longest and still valid DR. In this case the next longest valid DR is "ECG report". Thus, processor 14 selects the "ECG report" DR and forms an appropriate address for linking purposes. The above example is only exemplary and, for example, the process may be reversed whereby the shortest DRs are sought and as additional text is entered, processor 14 determines if longer DRs are entered. If additional text does not correspond to a longer DR, the shorter DR is identified and a corresponding address formed.

Another problem which can occur when attempting to form links between references in one record and records associated with the references is that DRs may overlap. For example, assume that two supported DRs consist of the phrases "admission ECG" and "ECG report" (i.e., here it is assumed the phrase "admission ECG report" is not supported). In this case, if the phrase "admission ECG report" appears in a record, which of the two supported DRs should be selected for addressing purposes is unclear and selecting both would be confusing.

To deal with this problem RRS 7 imposes another rule on processor 14 operation which requires processor 14 to select the first of several DRs when DRs overlap. Thus, in the present example, processor 14 would select DR "admission ECG" and would discard DR "ECG report".

Figure 5:
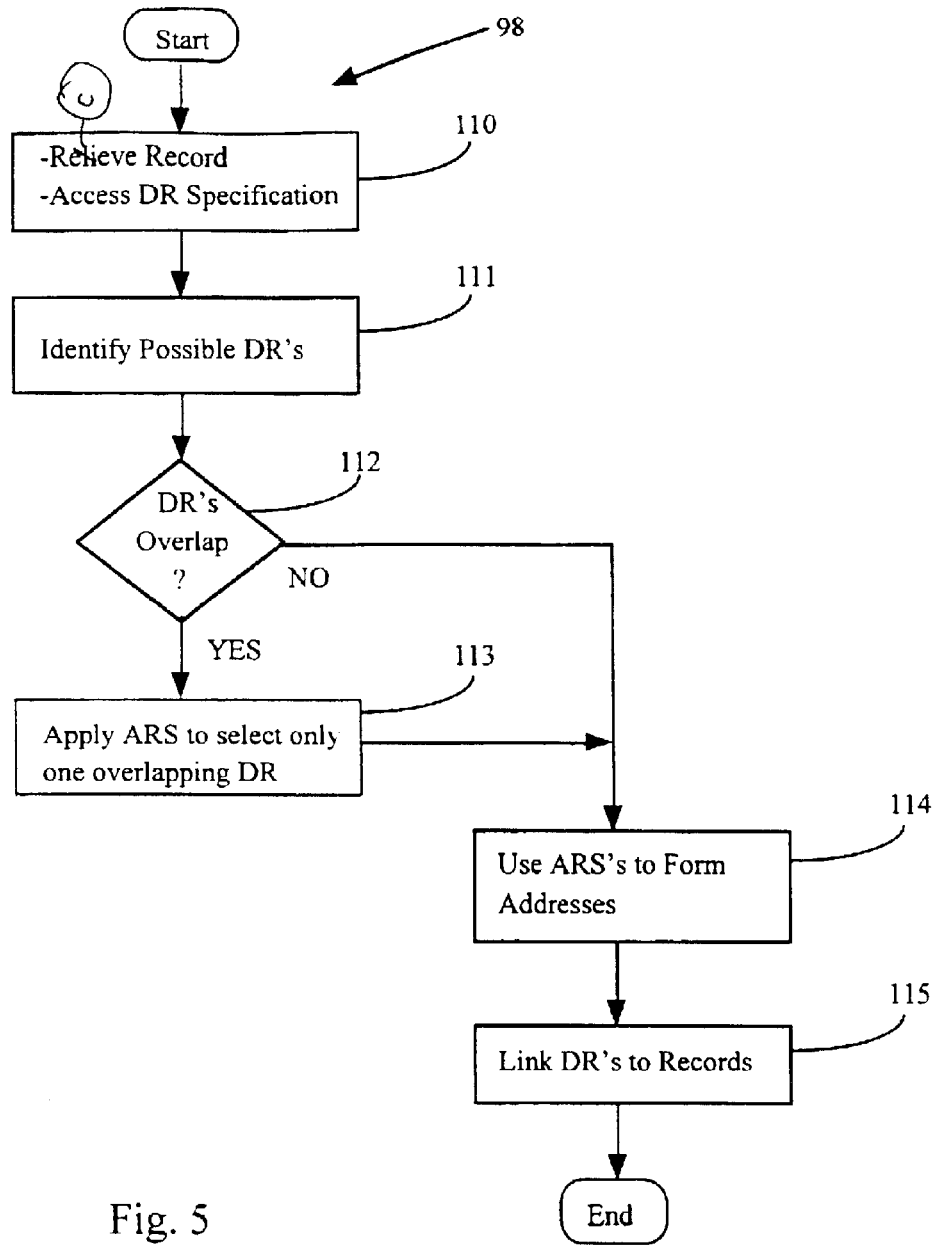
FIG. 5 is a flowchart illustrating an inventive method.

An exemplary DR selection process 98 which resolves ambiguity where DRs overlap is illustrated in FIG. 5. Referring also to FIGS. 2 and 3, at block 110 processor 14 receives a record and accesses DR specification 4. At block 111 processor 14 determines if any DRs overlap. Where no DRs overlap control passes to block 114 where processor 14 uses an ARS from table 5 to form addresses for each DR and at block 115 processor 14 links DRs to associated records via the created addresses. Where DRs overlaps at block 112 control passes to block 113 where processor 14 applies RRS 7 to select only one DR from each set of overlapping DRs. Then control passes to block 114 where addresses are only generated for unambiguous DRs which do not overlap.

The '177 application also contemplates a more complex system which supports additional levels of referencing for linking purposes. To this end, the '177 application recognizes that a single DR may be modified by any of several different modifier references (MRs) such that each DR/MR combination refers to a specific and distinct record or record segment and is correlated with a specific record or segment address. For example, a DR may comprise the term "ECG" while one MR may be "previous" and another MR may be "admission" so that DR/MR combinations include each of "admission ECG" and "previous ECG.".

Figure 6:
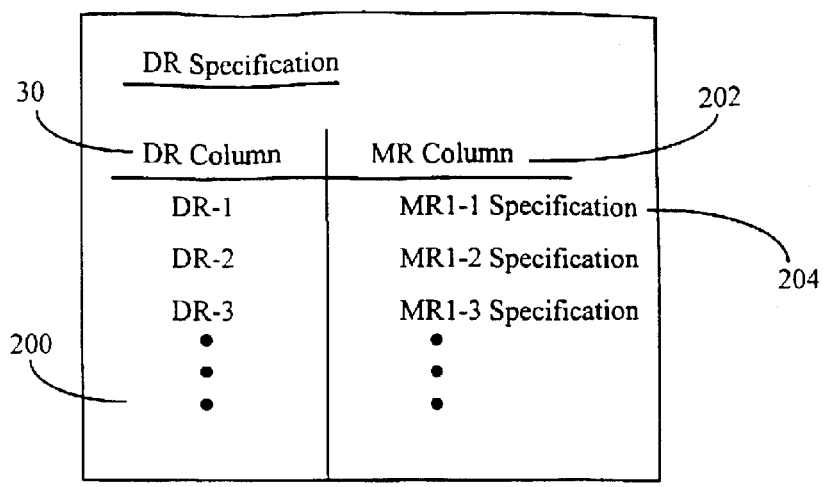
FIG. 6 is a schematic diagram illustrating another DR specification.

Referring to FIG. 6, to support DR/MR combinations a slightly different DR specification 200 is required. Specification 200, like table 5, includes a DR column 30 which lists all possible DRs. However, instead of including an ARS column 32, specification 200 includes an MR specification column 202 which lists a separate MR specification for each DR in column 30. Exemplary MR specifications in column 202 are MR1-1, (i.e. 204) and MR1-2 which correspond to DR-1 and DR-2, respectively. The first number in each MR specification reference (i.e., "1" in MR1-1) indicates a first level (levels are described in more detail below) MR and the second number (i.e., "2" in MR1-2) indicates which DR the MR reference corresponds to. For example, MR1-1 is a first level MR and corresponds to DR-1 while MR1-2 is a first level MR and corresponds to DR-2.

Figure 7:
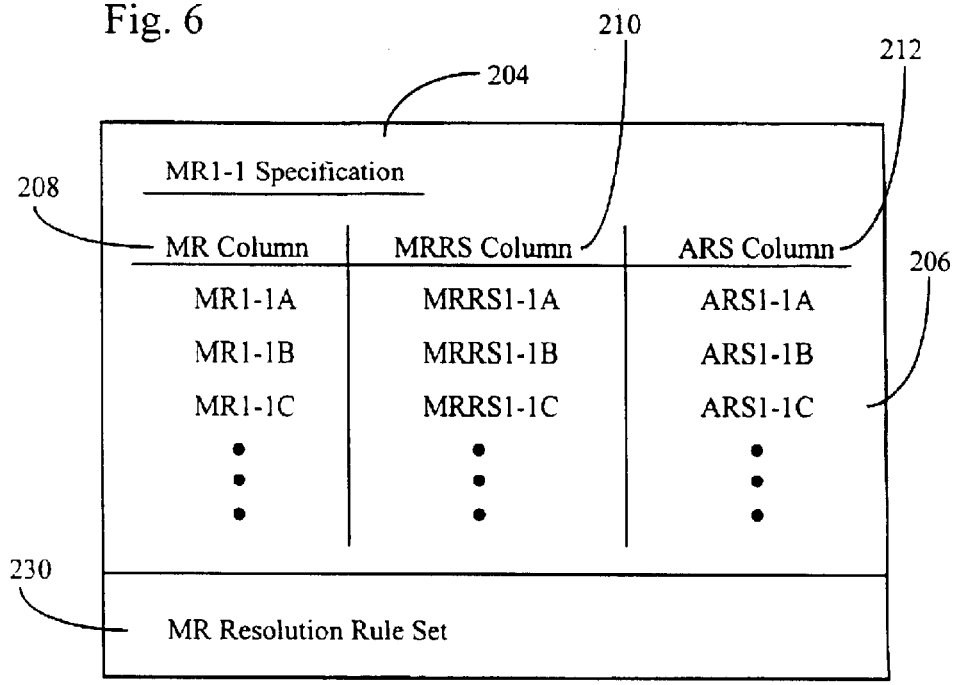
FIG. 7 is an expanded schematic diagram of one of the MR specifications of FIG. 6.

Referring also to FIG. 7, specification 204 includes an MR1-1 table 206 and an MR resolution rule set (RRS) 230. Table 206 includes an MR column 208, an MR rule set (MRRS) column 210 and an ARS column 212. Column 208 lists all MRs which may modify DR-1. For example, where DR-1 is "ECG", MR1-1A may be "previous", MR1-1B may be "admission", MR1-1C may be "report" and so on. In column 208, different MR1-1s are identified by distinct capital letters (e.g., A, B, etc.) following the reference MR1-1. Similar referencing distinguishes MRRSs and ARSs in columns 210 and 212, respectively.

Column 210 lists a separate MRRS corresponding to each MR in column 208. For example, where MR1-1A is "previous", MRRS1-1A may indicate that, for MR1-1A to modify DR-1, the term "previous" must appear within five words before or after DR-1 within the examined document. Other MRRSs are contemplated including MRRSs which include natural language processing and like functions.

ARS column 212 lists a separate ARS which are like the ARSs in FIG. 4, a separate ARS corresponding to each MR in column 208. For example, ARS1-1A corresponds to MR1-1A and indicates an address format for the DR/MR combination DR-1/MR1-1A.

Where a system supports DR/MR combinations, the above described linking process is a bit more complex. To this end, when a DR is identified by processor 14, processor 14 next attempts to determine if an MR corresponding to the DR and which meets the criteria required by the corresponding MRRS is present in the record being searched. Thus, for example, when processor 14 identifies DR-1, processor accesses table 200, identifies specification 204 (see FIG. 6) and searches for each MR in column 208 (see FIG. 7) according to corresponding MRRSs in column 210. When an MR which meets the criteria set forth in a corresponding MRRS is identified, processor 14 retrieves the ARS corresponding thereto and proceeds to construct an address corresponding to the DR/MR combination. Thereafter system supported linking is performed.

Figure 8:
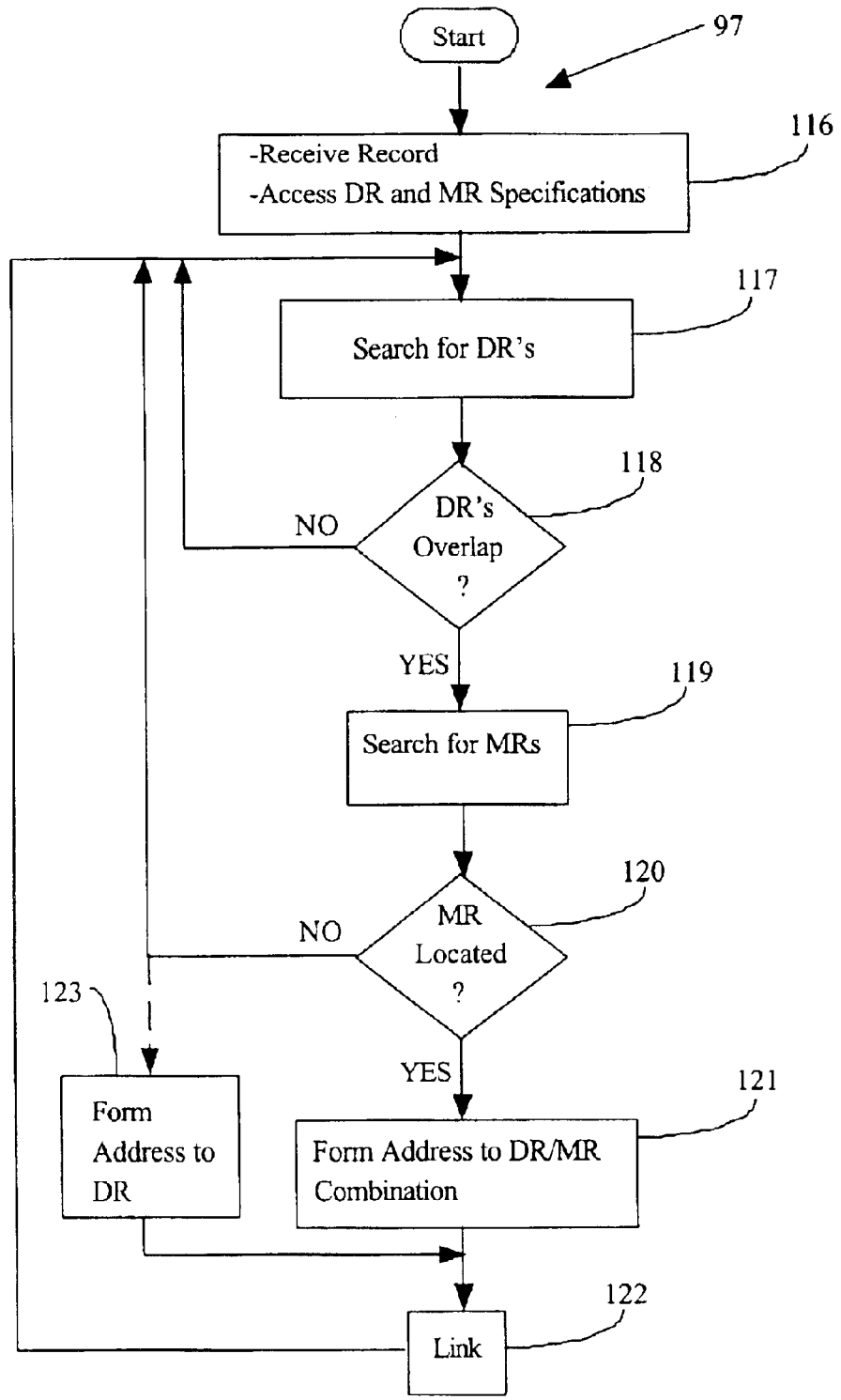
FIG. 8 is a flowchart illustrating a method for identifying DR/MR combinations in a record and forming an address corresponding thereto.

An exemplary DR/MR selection process 97 is illustrated in FIG. 8. Referring also to FIGS. 2, 6 and 7, at block 116 processor 14 receives a record and accesses DR and MR specifications 200, 204, respectively. At block 117 processor 14 searches for DRs and, if no DRs are located, loops back at block 118 until a DR is located. At block 119, after a DR is located, processor 14 searches for each MR in column 208 which may modify the located DR. If no modifying MR is located at block 120, control loops back to block 117. At block 120, when an MR which meets MRRS criteria is located, control passes to block 121 where an address corresponding to the DR/MR combination is formed. Linking again occurs at block 122 and control passes to block 117 to search for another DR.

Systems are also contemplated which support both DRs and DR/MR combinations. For example, where DR-1 is term "ECG" and MR1-1A is term "previous", a specification like specification 4 in FIG. 3 and a specification like specification 200 in FIG. 6 may both be supported. In this case, where DR-1 is identified in a record and MR1-1A is not identified, a link to the record or segment associated with DR-1 may still be made. Similarly, when the DR-1/MR1-1A combination is identified, a link to the record or segment associated therewith can be made. In FIG. 8, this alternate embodiment is represented by block 123 where, after a DR is identified and no MR is located, instead of looping back to block 117 to search for another DR, processor 14 forms an address corresponding only to the DR prior to linking at block 122. Unfortunately, as in the case where a long DR may include a short DR and additional text, here the DR/MR combination includes the base DR and ambiguity may result.

Therefore, as in the case of multiple length DRs, here, RRS 230 imposes a rule which specifies which of two DR/MR combinations or which of a DR/MR combination and a DR should be selected instead of the other when one combination includes the other and additional text. In this regard, the term "specifying reference" (SR) is used to refer generically to each of a DR and a DR/MR combination. The preferred rule is that the longest SR chosen. Once again, the manner in which the longer of two SRs is chosen is irrelevant and many different methods are contemplated.

In addition to the problem of dealing with SRs wherein a long SR includes a short SR and additional text, as with DRs, SRs may overlap and cause confusion. This is particularly true as MRRSs typically will specify, among other things, a range of terms about a corresponding DR which should be examined to identify an MR. Thus, where typical ranges are five terms before and after, the likelihood of overlap may be relatively high.

In this case it is contemplated that RRS 230 also includes rules for eliminating uncertainty when two SRs overlap. A preferred RRS 230 specifies that when a SR is identified, MRRSs corresponding to possible subsequent DR/MR combinations are modified such that the MRRS ranges are limited by the DR or MR in the identified SR and which is adjacent the subsequent possible combination. For example, assume a first combination including the MR "report" within two terms of the DR "ECG", a second DR/MR combination includes the MR "post-op" within five terms of the DR "X-ray image" and a record segment includes the phrase "The ECG post-op report and the X-ray image". In this case, when processor 14 considers the phrase, processor 14 first recognizes the "ECG report" DR/MR combination and forms an address therefore for linking purposes.

Thereafter, processor 14 accesses specification 200 (see FIG. 6), recognizes DR "X-ray image" in the record being searched, accesses the MR specification 204 associated with DR "X-ray image" and, for each MR in column 206, prior to searching for the MR, modifies the MRRS search range associated therewith as a function of the "ECG report" DR/MR combination if necessary. In the present case, because DR "X-ray image" is within three terms (i.e., "report and the X-ray image") of MR "report", the MRRS range preceding DR "X-ray image" is reduced from five terms to two terms. Thus, in this case, the DR/MR combination "post-op X-ray image" is not identified despite due to formation of the "ECG report" combination.

Another problem which may arise may be that a single DR instance may possibly be included in two overlapping DR/MR combinations. For example, the DR "ECG" may be modifiable by both MRs "report" and "admission" and a phrase "admission ECG report" may appear in a record. In this case which of two DR/MR combinations should be selected for linking may cause confusion. Here, as in the case of overlapping DRs, RRS 230 includes a rule which causes the first of two DR/MR combinations to be selected when a single DR instance is included in overlapping combinations.

Yet one other problem is that, in some cases, it might be desirable to have a single MR modify two DRs and in that case, each of two DR/MR combinations, although overlapping, should be linked to corresponding records and selectable by a system user. For example, assume a record includes the phrase "See the ECG image and x-ray image of Jan. 15, 1996. . ." where "ECG image" and "X-ray image" are each DRs and date "Jan. 15, 1996" is an MR which may modify each of the two DRs.

In this case, MR "Jan. 16, 1996" may be meant to modify only "X-ray image" or both "X-ray image" and "ECG image." An ambiguous situation occurs. Among others, the present invention contemplates three general solutions for dealing with such ambiguity.

Figure 25:
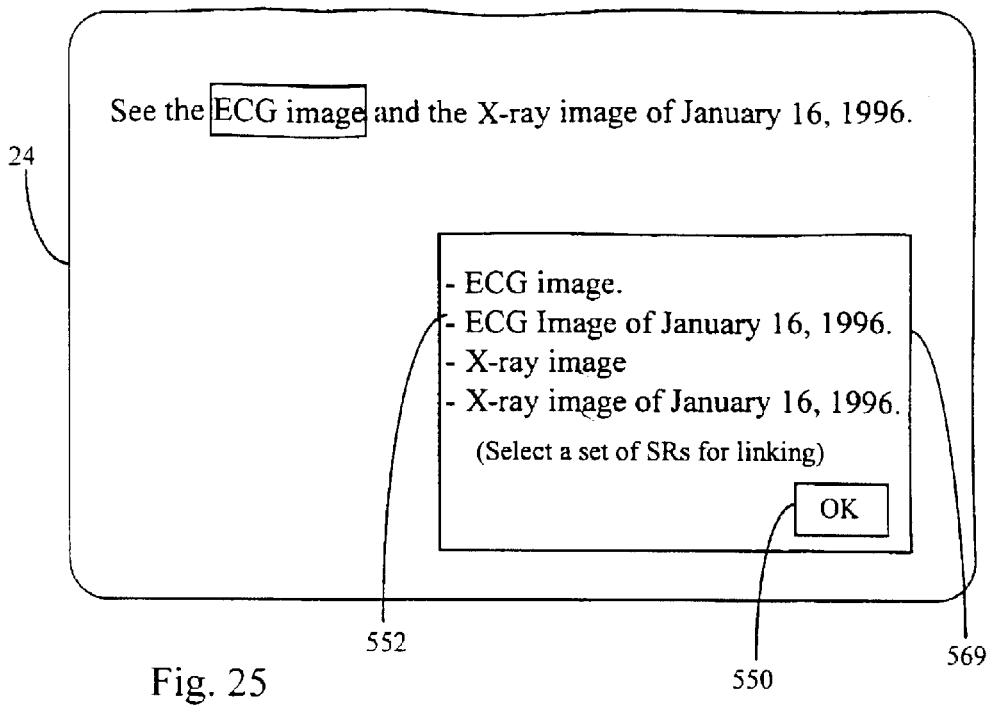
FIG. 25 is a schematic diagram illustrating an SR choice box according to the present invention.

First, where ambiguity occurs, processor 14 may query a system user to determine which, if any, DR/MR combinations and which DRs should be used for linking purposes. In the present example, this is accomplished by, when a system recognizes potentially overlapping SRs, providing a selection box to the user indicating all possible SRs (i.e., DRs or DR/MR combinations) associated with a phrase. Referring to FIG. 25, box 550 indicates four possible SRs including "ECG image", "ECG image of Jan. 16, 1996", "x-ray image" and "x-ray image of Jan. 16, 1996." In addition an "OK" icon 569 is provided. After highlighting a set (e.g., two of them, all of them, none of them, etc.) of SRs to be formed when OK icon 569 is selected, addresses corresponding to all selected SRs are formed and links are made. Where selected SRs overlap, upon subsequently selecting an overlapping SR, a subsequent choice step is supported by processor 14 as described in more detail below.

Second, where ambiguity occurs, processor 14 may automatically identify every possible SR combination generating addresses for each and forming links for each. Thus, in FIG. 25, a separate link to each of the four SRs listed would automatically be formed without providing an option to a system user. In this regard, processor 14 may, when an SR is identified, form an address to a corresponding record and, prior to forming a link for subsequent selection purposes, determine if a corresponding record actually exists. Where a record does not exist, the link is foregone.

After links are formed and when a record including highlighted SRs is presented to a user, upon designation of an overlapping SR, processor 14 provides a choice box for a user. Herein the term "designate" is used to refer to a process whereby a system user may point to text on a display screen(e.g., via a mouse controlled cursor) without actually taking an affirmative step to select the text. This action is also referred to in the industry as "hovering over" an icon or object. For example, a user may place a pointing arrow icon on an SR without selecting the SR.

Figure 26:
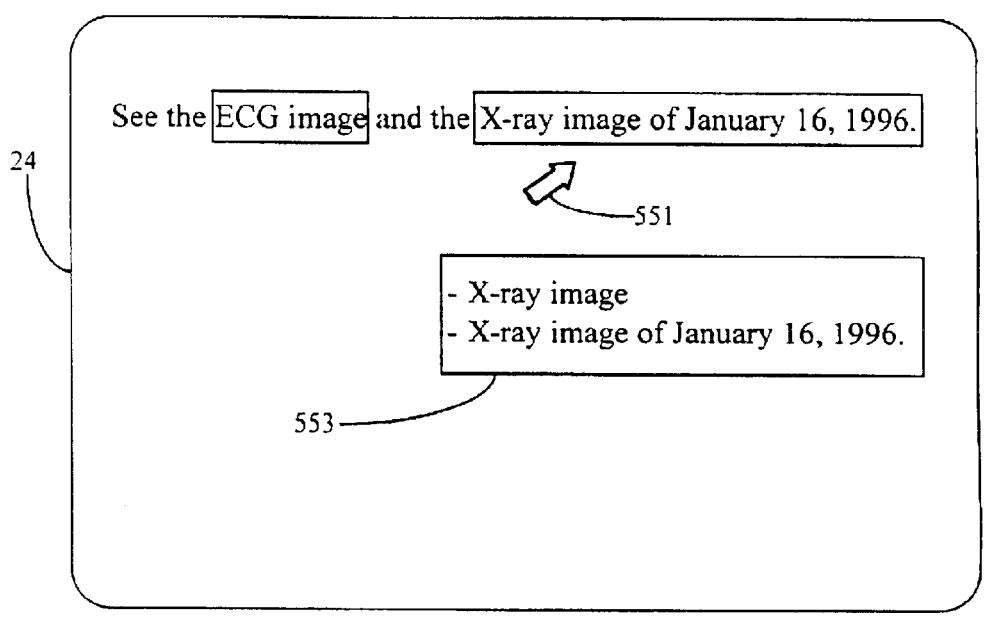
FIG. 26 is a schematic diagram illustrating another choice box according to the present invention.

Referring to FIG. 26, boxed text indicates highlighted text corresponding to one ore more SRs. Assuming each of "X-ray image" and "X-ray image of Jan. 16, 1996" are overlapping SRs which correspond to different records, when the phrase "X-ray image" is designated via a mouse controlled cursor 551 or the like, processor 14 automatically provides a selection box 553 including a list of possible SRs for linking. In this case the list includes "X-ray image" and "X-ray image of Jan. 161, 1996." One list SR can be selected via appropriate mouse activation to form a desired link.

Third, when ambiguity occurs, processor 14 may be provided with intelligence which enables processor 14 to determine which of several different SRs should be supported by addressing and linking capabilities. For example, in one embodiment, as above, the general rule that the longest of two possible SRs should be supported and the shorter discarded is assumed. In another embodiment, it is assumed that where two or more DRs appear in an inclusive (i.e., the last and second last DRs in the list are separated by the word "and") or an exclusive (i.e., the last and second last DRs in the list are separated by the word "or") list and the last DR in the list is modified by an MR which follows the last DR, each of the DRs in the list should be modified by the MR independent of whether or not the MR meets the MRRS requirements for a specific DR. For instance, in the present example where a date MR may modify each of DRs "ECG image" and "X-ray image" but date "Jan. 16, 1996" is separated from phrase "ECG image" by terms which place the date outside the MRRS range for phrase "ECG image," because phrases "ECG image" and "X-ray image" are separated by term "and" and date MR "Jan. 16, 1996" follows DR "X-ray image" and modifies "X-ray image," it would be assumed DR "ECG image" is also meant to be modified by the date MR (i.e., "Jan. 16, 1996").

It is contemplated that processor 14 would support many other rules such as what to do when an MR precedes one DR in a list of DRs or what to do when an MR precedes a DR list and so on. In addition, it is contemplated that combinations of each of the three approaches above, may also be supported. For example, in some cases processor 14 may be programmed to automatically select one of several different SRs, in other cases processor 14 may be programmed to automatically form all possible SR addresses and links while in other cases processor 14 may be programmed to provide SR options to a system user. Moreover, other lists which are neither inclusive nor exclusive may be recognized by the processor which may distribute the effect of a proximate MR to each DR in such a list.

Figure 27A:
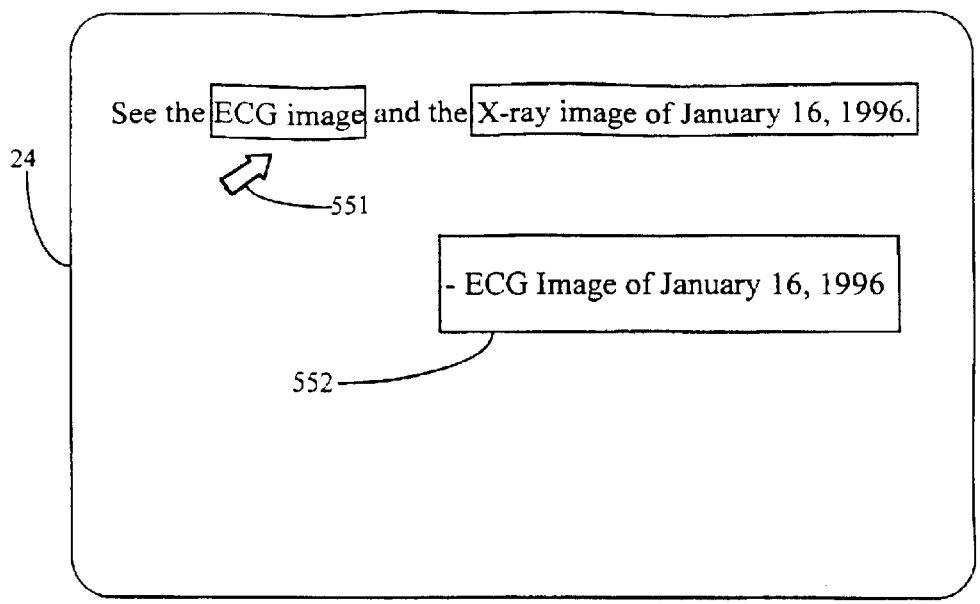
Figure 27B:
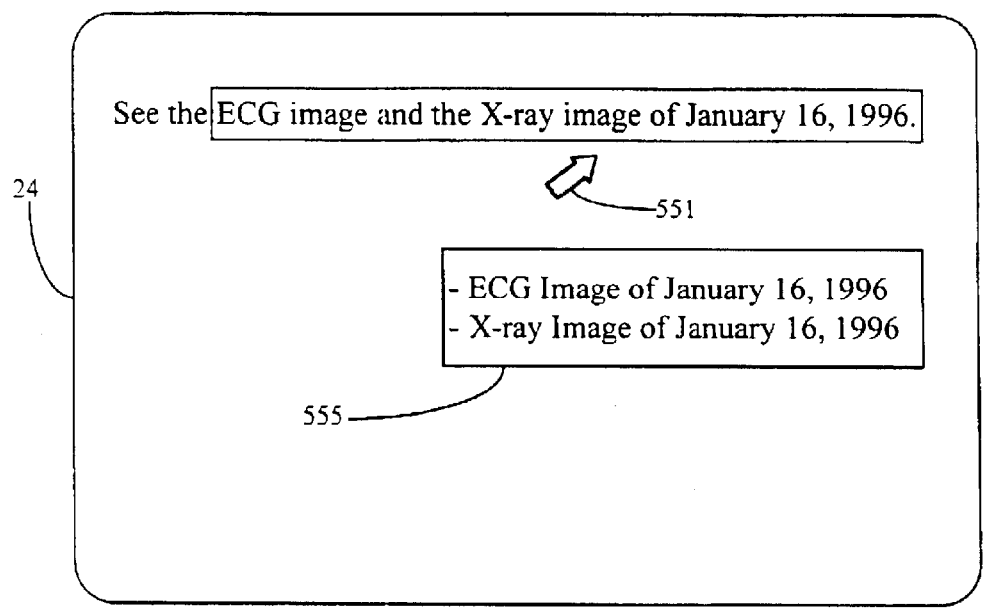
FIG. 27b illustrates a choice box.

When SRs overlap (e.g., one MR modified each of two DRs) and are displayed, a tool must be provided to enable a user to separately select each SR from a record despite the overlap. To this end, referring to FIG. 27a, the exemplary phrase "See the ECG image and X-ray image of Jan. 16, 1996. . . " is illustrated as it would appear in one embodiment of the invention after highlighting and linking. In FIGS. 27a–27b, a box around text indicates highlighting. Thus, in FIG. 27a phrases "ECG image" and "X-ray image of Jan. 16, 1996" are both highlighted. In this instance, it is assumed date "Jan. 16, 1996" modifies each of phrases "ECG image" and "X-ray image." Nevertheless, because the phrase "ECG image" is separated from MR "Jan. 16, 1996," as illustrated, a record observer would not recognize the modifying relationship.

Here, when a mouse controlled cursor 551 is used to designate a DR which is separated from an associated MR, processor 14 provides an SR description box 552 to help the user navigate system records. For example, referring still to FIG. 27a, when phrase "ECG image" is pointed to prior to selection thereof, processor 14 provides description box 552 adjacent phrase "ECG image" showing the SR (i.e., "ECG image of Jan. 16, 1996"). Thereafter, selection via a mouse or the like links the user to the corresponding ECG image of Jan. 16, 1996.

As another example, when two DRs are separated by the word "and" and one of the DRs is modified by an MR such that it will be assumed both DRs are to modified by the MR, processor 14 may be programmed to highlight the entire inclusive phrase "ECG image and X-ray image of Jan. 16, 1996" as illustrated in FIG. 27b. In this case, when a mouse controlled pointing icon 551 is used to designate any part of the highlighted phrase, a selection box 555 opens which lists all possible DR/MR combinations in the phrase. In this case the possible combinations include "ECG image of Jan. 16, 1996" and "X-ray image of Jan. 16, 1996." Thereafter, activation of an appropriate mouse button causes combination selection and linking as described above.

The invention also contemplates a system which supports various MR levels such that one or more MRs can be further qualified or modified by another MR in another MR level. Thus, for example, where DR-1 is "ECG" and MR1-1A is "previous", a second level MR, MR2-1A, may be "record" while another second level MR, MR2-1B, may be "heartbeat". In this case when a DR/MR1-1A combination is identified, processor 14 searches a range of terms adjacent MR1-1A to identify one of the second level MRs (i.e., MR2-1A, MR2-1B, etc).

To support this type of system the DR specification would be essentially identical to the specification of FIG. 6. However, the MR specification would be different than the specification of FIG. 7. Referring to FIG. 9, an MR1-1 specification 240 which supports two MR levels is illustrated. Specification 240 includes an MR table 242 including an MR1-1 column 244, an MRRS1-1 column 245 and an MR2 specification column 246. Column 244 includes a list of all MRs which may modify DR-1 (see FIG. 6).

Column 245 includes a list at separate MRRSs corresponding to each MR1-1 in column 242. For example, where MR1-1A is "previous", MRRS1-1A may indicate that, for MR1-1A to modify DR-1, the term "previous" must appear within five words before or after DR-1 within the examined document. Other MRRSs are contemplated including MRRSs which include natural language processing and like functions.

In addition, the MRRS range may be any range including a text fragment, a sentence segment in which a DR appears, a sentence in which a DR appears, a paragraph in which a DR appears, a table cell in which a DR appears or an entire record (e.g. a patient ID# which appears once at the top of a record may modify every DR in the record).

Column 246 includes a separate MR2 specification for each MR1-1 in column 242. An exemplary MR2 specification is identified by numeral 250. Referring also to FIG. 10, specification 250 includes an MR table 252 and an M2 resolution rule set (RRS) 254. Table 250 includes an MR2-1 column 256, an MRRS2-1 column 258 and an ARS2-1 column 260. Referring to FIGS. 9 and 10, column 256 lists all MR2-1s which may modify MR1-1A. For example, where DR-1 is "ECG" and MR1-1A is "previous", MR2-1A may be "report".

Column 258 lists a separate MRRS corresponding to each MR2-1 in column 256. For example, where MR2-1A is "report", MRRS2-1A may indicate that, for MR2-1A to modify MR1-1A, the term "report" must appear within five words before or after MR1-1A within the examined document provided intervening words are not syntactically relevant or bring up new subject matter.

ARS2-1 column 260 lists ARSs which are like the ARSs in FIG. 4, a separate ARS corresponding to each MR2-1 in column 256. For example, ARS2-1A corresponds to MR2-1A and indicates an address format for the DR/MR combination DR-1/MR1-1A/MR2-1A.

Where a system supports DR/MR1/MR2 combinations, the above described linking process is more complex. To this end, when a DR is identified by processor 14, processor 14 next attempts to determine if an MR1 corresponding to the DR and which meets the criteria set forth in the corresponding MRRS1 is present in the record being searched. Thus, for example, when processor 14 identifies DR-1, processor 14 accesses table 200 (see FIG. 6) and table 242 (see FIG. 9), identifies specification 240 and searches for each MR1-1 in column 244 according to corresponding MRRS1-1s in column 245.

When an MR1-1 which meets the criteria set forth in a corresponding MRRS1-1 is identified, processor 14 accesses the MR2-1 specification associated with the identified MR1-1. In the present case it is assumed MR1-1A is identified and therefore processor 14 accesses specification 250 (see FIG. 10). Next, processor 14 attempts to determine if an MR2-1 corresponding to MR1-1A and which meets the criteria set forth in the corresponding MRRS2-1 is present in the record being searched. Thus, for example, when processor 14 identifies MR1-1A, processor 14 accesses specification 250, accesses table 252 and searches for each MR2-1 in column 256 according to corresponding MRRS2-1s in column 258. When an MR2-1 meets the criteria set out a corresponding MRRS2-1, processor 14 accesses an associated ARS2-1 in column 260 and proceeds to form an address to the DR-1/MR1/MR2 combination which is consistent with the address format specified by the ARS.

As in the cases of SRs which overlap or form parts of other SRs, where there are two or more MR levels, confusion due to overlap and common DRs and MRs among combinations result. Therefore, it is contemplated that RRS 254 includes rules which eliminate ambiguity when overlap and common terms occur. To this end, as in the other examples above, the preferred rules specify that when one SR is longer than another, the longer combination is selected and the shorter combination is discarded. In this regard, where a first SR is longer than a second and includes the second, processor 14 identifies the longer SR for linking purposes.

In addition, when one MRRS range searched extends into a previously identified DR/MR combination, the MRRS range corresponding to the one MRRS is restricted to terms which do not include the previously identified combination and when two combinations overlap the first is identified and the second is discarded.

While preferred resolution rule sets have been described above, the broadest aspect of the rule limitations is that at least some rules are provided to eliminate ambiguity in selecting DRs and DR/MR combinations for linking purposes. For example, many other resolution rule sets are contemplated. For instance, according to another limited resolution rule instead of identifying a first DR and discarding the second, where two DRs overlap, the second of two DRs could be selected and the first discarded. Similarly, instead of having a rule which always causes processor 14 to identify the longest SR at the expense of other SRs, the RRSs may specify exceptions. For example, where a first DR includes the phrase "admission ECG report" which may be modified by the MR "image" within three terms (i.e., the MRRS corresponding to MR "image" specifies a range of three terms before and after the DR), a second DR includes the term "X-ray" which may also be modified by the MR "image" within three terms and a record segment includes the phrase "Upon a perusal of the admission ECG report, X-ray image, and examination notes . . . ", if processor 14 always selected the longest SR and disregarded the rest the identified SRs would be "admission ECG report image" and "X-ray". The combination "X-ray image" would be discarded.

Instead, an exception may be to limit an MRRS search range by a second DR if a first DR is identified and the second DR appears between the first DR and an MR. In this case, the term "X-ray" would limit processor 14 examination range to locate MR "image" and the result would be two linking references including "admission ECG report" and "X-ray image", an outcome which is more likely to be intended. A rule similar to this rule may also be included as an exception where a noun falls between a DR and a possible MR where the noun is not a DR. For example, in the phrase "ECG and ultrasound image" where "ECG" is a DR, "image" is an MR and ultrasound is not a DR, the term "ultrasound" should still delink the DR and MR such that the SR "ECG image" is not recognized.

In addition, the invention contemplates a "null" link wherein a DR such as "ultrasound" above may be defined without a corresponding address so that, while the DR is recognized, no link is formed. This feature enables an MR and another DR which are separated by the "ultrasound" DR to still be recognized as related. For instance, in the example above "ultrasound" may correspond to a null link such that when the phrase "ECG and ultrasound image" is identified, each of ECG and ultrasound are modified by the "image" MR, an "ECG image" link to an address is formed and a null address is linked to "ultrasound image".

One other preferred rule is that, when an SR is selected for address and linking purposes, the process of searching the record for additional SRs is limited by the previously selected SR. For example, where the phrase "previous ECG image and the X-ray image . . . " is encountered, processor 14 selects the phrase "previous ECG image" as a first SR and thereafter limits SR searches such that the searches do not include the selected phrase. Hence, the term "previous" will not, in this example, be considered a possible MR for modifying DR "X-ray image."

Another preferred rule is that when one MR may be included in two SRs, processor 14 should identify the SR including the DR which is closest to the MR for linking purposes and should select the related SR to form an address.

It should be appreciated that while the inventive methods are described or including first searching for DRs and then for MRs, the invention also contemplates systems wherein an MR may be sought first and a DR thereafter.

2. Creating Links Using a Table and Resolution Rules

While the ARSs described above are extremely useful, it has been recognized that other simpler tools can be used to form links between DRs in one record and other records referenced and associated with those DRs. To this end, the '177 reference teaches one system wherein specific DRs can be linked to specific records or record segments which are stored at known addresses. When a DR is assigned to a segment, the DR is correlated with the segment address and the DR and address are stored in a lookup table. Thereafter, during a linking procedure, a processor accesses the lookup table and searches a record for each DR in the table. When a DR is located, the processor links the DR in the record to the record at the corresponding address.

It has also been recognized that pre-existing DR/address tables may be used for linking purposes. Referring now to FIG. 11, an exemplary DR/address lookup table 270 is illustrated. Table 270 is comprised of two columns including a DR column 272 and an address column 274.

Column 272 includes a list of DRs. Column 274 includes a separate address for each DR in column 272. While it is contemplated that virtually any record may be addressed in column 274 and associated with a DR in column 272, in most cases the records associated with addresses in column 274 will be of a generic or semi-generic nature. For example, in the context of a medical facility, records associated with addresses in column 274 may be tutorials or informational bulletins. For instance, DR 276 is "ECG procedure" and the corresponding address 278 is the address of a bulletin which can be consulted to learn about an ECG procedure at the medical facility. As another example, DR 280 is "breast cancer bulletin" and the corresponding address 282 is the address of a bulletin which can be consulted to learn about recent developments in breast cancer research.

In operation, assuming the link creating processing feature is activated. As a physician enters information into a record, when the physician types in the phrase "breast cancer bulletin", the processor matches DR 280 to the typed phrase, identifies address 282 and forms a link between the DR in the record and the record indicated by address 282.

As in the case of systems which support ARSs, in systems which include DR/address tables, additional complexity is contemplated wherein DRs can be modified by one or more levels of MRs such that several different DR/MR combination levels may be supported. Extension of the DR/MR principles taught above should be easy for one of ordinary skill in the art.

In addition, it is contemplated that one SR may include or overlap another SR. In an including or overlapping situation, as in systems which support ARSs, it is contemplated that rules are provided which enable unambiguous selection of one SR and different treatment of the other. As above, the different treatment may constitute disregarding the other DR or combination or, in the case of a DR/MR combination, may constitute modifying an MRRS search range as a function of overlapping DRs and MRs.

3. Tag Enabling

While automatic address linking features described above are extremely useful, unless specific information within a record is separately addressable via conventional addressing protocols, such features do not facilitate recognition of specific information in a record after the record has been retrieved. For example, assuming each patient post-op record includes an abstract indicating the general nature of a surgery and the perceived outcome, if a physician wishes to view a record abstract, with conventional address linking systems, the physician has to provide the record address and, when the record is retrieved, then has to independently review the record to identify the abstract. While this may not be extremely burdensome in the case of an abstract which would likely have a known position (e.g., near the front or rear) within a record, other information types would likely be much more difficult to locate. In addition, where the physician must locate many (e.g., 10) different segments of information in a record, the task of manually locating information may prove daunting.

According to the present invention the concept of automatic linking is taken one step further and includes a system which automatically provides "tags" within records which can be used by processing applications to distinguish different information types within the record. To this end, generally, processor 14 is equipped to recognize characteristic sets which correspond to different record segments and, when a specific segment is identified, can place tags around the segment which are recognizable by other applications. Preferred tags are XML tags although any other tags which are recognized by a suitable application may be used and are certainly contemplated. Referring to FIGS. 2 and 12, database 2 may include an XML specification 290 including at least an XML rule set (XMLRS) column 292, an XML begin tag column 294 and an XML end tag column 296. A fourth column, an XML type column 298, is illustrated to simplify this explanation but may not be required in an actual system.

XML type column 298 lists all information types which XML specification 290 supports and indicates the types via descriptive names. For example, in the case of a medical facility, column 298 may include a patient ID type 300, heart rate type 302, image type 304, abstract type 306, diagnosis type 308, prescription type 310, etc.

Column 292 includes a separate XMLRS for each XML type listed in column 298. The XMLRSs provide rules to be used by processor 14 to determine if information within a record segment is of the corresponding XML type. For example, in the case of XML type patient ID 300, referring also to FIG. 13, XMLRS 312 includes a variable character string 314 which has a form recognizable as a patient ID. In the present case it is assumed that each patient at a medical facility is identified by an unambiguous and distinct character string including two numbers followed by two letters which are in turn followed by five numbers. In XMLRS 314 a "#" character indicates a digit from 0 through 9 while an "X" character indicates a letter. The first two characters are reserved for a year indication (e.g., 99 for 1999, etc.) The third and fourth characters are reserved for first and last name initials (e.g., Mary Jones would be MJ). The final five characters indicate a unique consecutively assigned number provided via an admit, discharge, transfer (ADT) system (not illustrated) when a patient is admitted to the facility. In this case the ADT system begins with a "00001" number at the beginning of a new year and it is assumed that the facility admits less than 100,000 patients each year.

Figure 14:
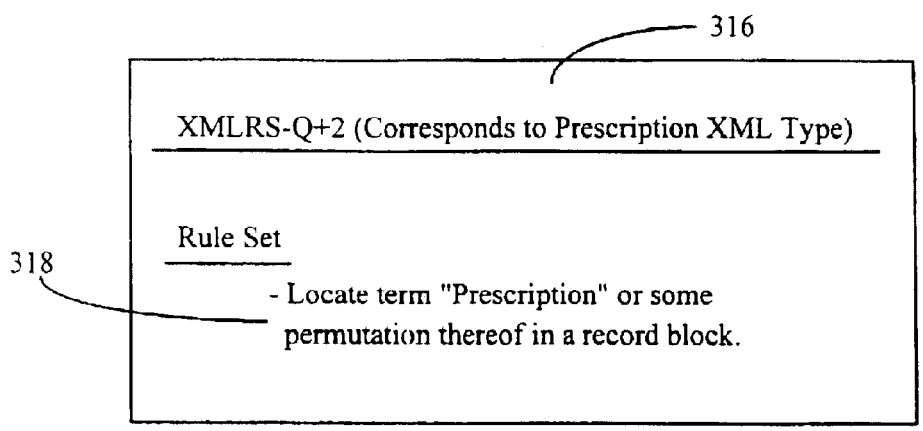
FIG. 14 is a schematic diagram of another exemplary XML rule set XMLRSQ+2 of FIG. 12.

As another example, referring to FIGS. 12 and 14, an XMLRS 316 corresponding to the prescription XML type 310 is illustrated. In this case, it is presumed that the medical facility has many different electronic forms which may be used to prescribe a medication or a procedure and that each form has a different format including several information blocks. For example, a first form may include a block for prescription indication at the top of the form while a second form includes a block for prescription indication at the bottom of the form. It is also presumed that a generic form enables the physician to indicate a prescription in any of several different form blocks. For instance, the generic form may include five blocks and the physician may select any of the five different blocks for indicating a prescription, other examination information being provided in one or all of the additional four blocks. Furthermore, it is presumed that in any case where a prescription is ordered, the physician must use (i.e., type in) the term "prescription" in conjunction with the prescription.

In this case XMLRS 316 (i.e., KMLRS-Q+2) includes the rule that, to identify a prescription, processor 14 must locate the term "prescription" within a form block. When the term "prescription" is identified, the processor 14 recognizes the information with the block as a prescription, the prescription beginning at the beginning of the block and the prescription ending at the end of the block.

Referring again to FIG. 12, column 294 includes a begin tag BT corresponding to each XML type listed in column 298 which can be inserted into a record to indicate the beginning of information of the type in column 298. For example, tag BT-1 corresponding to XML type 300 (i.e., patient ID) may be "<patient ID>" while tag BT-2 corresponding the XML type 302 (i.e. heart rate) may be "<heart rate>".

Column 296 includes an end tag ET corresponding to each XML type listed in column 298 which can be inserted into a record to indicate the end of information of the type in column 298. For example, tag ET-1 corresponding to XML type 300 (i.e., patient ID) may be "</patient ID>" while tag ET-2 corresponding the XML type 302 (i.e. heart rate) may be "</heart rate>".

Figure 13:
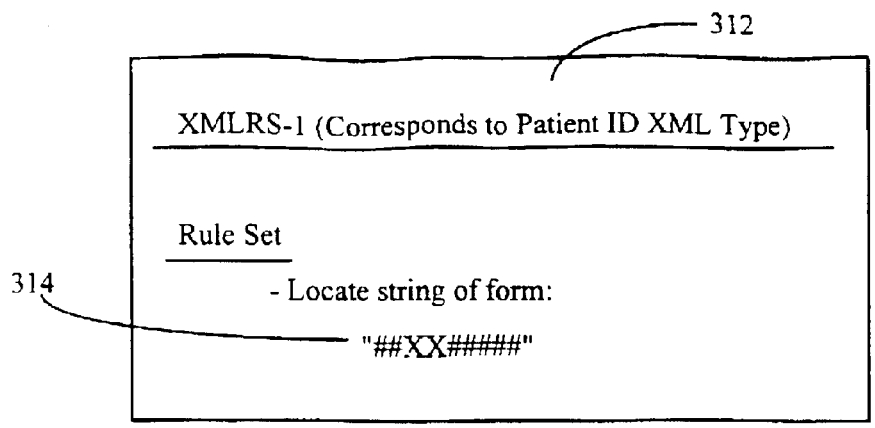
FIG. 13 is a schematic diagram of an exemplary XML rule set XMLS-1 of FIG. 12.
Figure 15:
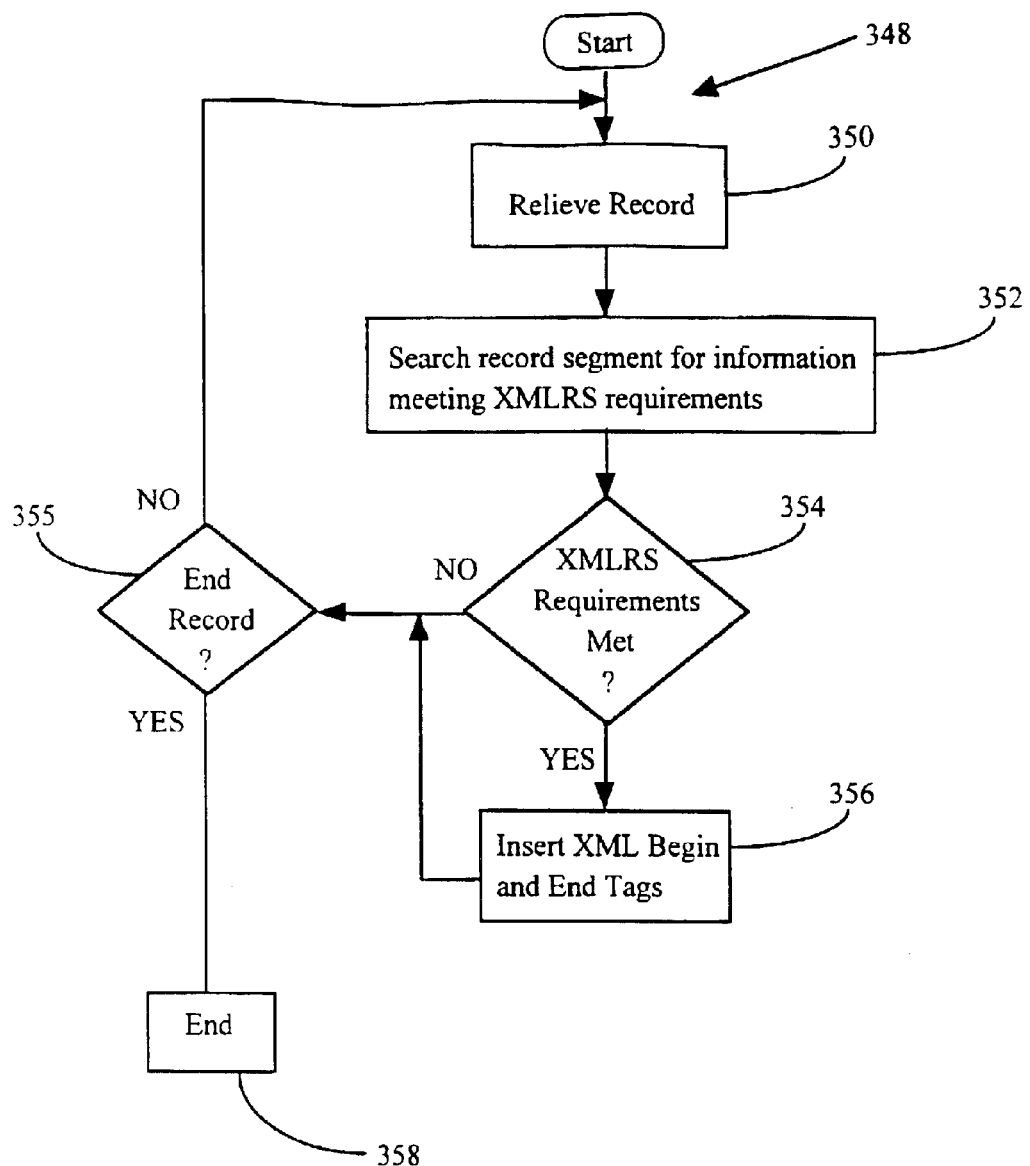
FIG. 15 is a flow chart illustrating an inventive method for identifying record segments for XML tagging.

Referring to FIG. 15, an exemplary XML enabling procedure 348 is illustrated. Referring also to FIG. 2, at process block 350 processor 14 receives a record. In this example, the record may be received in any of several different manners including batch downloading to processor 14 or, where a physician is entering a record via a word processor, by receiving record segments in real time. Referring also to FIGS. 12 through 14, as the record is received or after the record is received, at block 352, processor 14 searches the record segment by segment in accordance with the XMLRSs in column 292 to identify any information segments which meet the criteria specified in the XMLRSs. Receive At decision block 354, if no XMLRSs are satisfied by a currently examined segment, at decision block 355 processor 14 determines whether or not the previously examined segment is the last segment in the document and, if so, ends the XML searching function by proceeding to block 358. If there are additional record segments, processor 14 moves onto the next consecutive segment in the record by looping back to process block 352.

At process block 356, when an XMLRS is satisfied at block 354, processor 14 accesses corresponding begin and end tags in XML specification table 290 (see FIG. 12) and inserts corresponding XML begin and end tags into the record before and after the examined segment, respectively. Thus, in the present example, where a patient ID is identified, processor 14 inserts the begin tag patient ID<patient ID> and the end tag patient ID</patient ID> into the record before and after the identified ID, respectively. As known in the art, although inserted in the record, the XML tags are invisible to a record reader during normal record examination and are typically only recognized by a software application equipped to recognize and use XML tags.

After tags have been inserted in a record to distinguish one segment from others, processor 14 control passes to decision block 355 where processor 14 again determines if the previously examined segment was the last segment and, if the previously examined segment was the last segment, control passes to block 358. If the previously examined segment was not the last record segment control passes back up to process block 352 where the next segment is considered.

Once every record segment has been considered in light of the XMLRSs and all XML tags have been inserted into the record, the record is stored. At this point the record is tag enabled meaning that the record can be used by a tag enabled software application to identify specific information within the record. For example, where an application is searching for a record abstract associated with a patient report, after the report is accessed, the application simply searches for the XML tags corresponding to the beginning and the end of the abstract and accesses the information therebetween.

While the examples above include relatively simple XMLRSs in the context of a medical facility, more complex XMLRSs are contemplated and nested XMLs are also contemplated. For example, in the case of a United States patent specification, it is known that each patent generally includes several different sections or segments such as an abstract, a background, a summary, a brief description of drawings, a detailed description, a set of claims, figures and so on. It is also known that each patent segment is generally earmarked by a heading which indicates the information included in the segment and that each segment ends where the next segment begins. For example, the abstract is typically earmarked with the term "Abstract" or with the phrase "Abstract of the Invention" while the brief description of the drawings is typically earmarked with the phrase "Brief Description of the Drawings" and the claims are earmarked with the term "Claims".

Moreover, it is also known that within each main specification segment, other subsections are often readily identifiable via the form of the specification or the like. For instance, separate claims within the claims section of a specification begin with a number and end with a period while separate descriptions of figures within the brief description of the drawings begin with the term "Fig." or the term "Figure" and end with a period or a semicolon followed by another term "Fig." or "Figure" or by another major patent heading (e.g., "Detailed Description of the Invention". Furthermore, it is known that certain patent sections are typically preceded and followed by other specific specification sections. Thus, for example, the summary usually follows the background and precedes a brief description of drawings.

An exemplary XML specification 360 which supports nesting and which can be used to automatically render a patent specification tag enabled is illustrated in FIG. 16 and includes a type column 362, an XMLRS column 364 and begin and end tag columns 366 and 368, respectively. Structure and operation of specification 360 is similar to structure and operation of specification 290 (see FIG. 12) and therefore, in the interest of simplifying this explanation, only unique features of specification 360 will be described here in detail.

In FIG. 16 patent specification XML types are listed in column 362 including, among others, a "brief description of the drawings" type 370 and a "claims" type 372. A separate XMLRS (XMLRS-5, XMLRS-7) is listed for each of types 370 and 372, respectively. For example, referring also to FIG. 17, exemplary XMLRS-5 corresponding to the brief description of the drawings includes rules requiring processor 14 to search, after a "Summary of the Invention" section of the specification and before the "Detailed Description of the Invention" section to locate a heading including the phrase "Description of the Drawings" or some permutation thereof (i.e., "Brief Description of the Several Views of the Drawings" identified using natural language processing) followed by at least one description of a figure or drawing. Thus, each XMLRS may include many different contingencies. In fact, some requirements may be weighted such that more detailed intelligence is reflected within the decision making process.

Referring to FIG. 18, exemplary XMLRS-7 corresponding to the claims includes the rules requiring processor 14 to search an entire specification for a claims section by searching for a title "Claims" (or some permutation thereof) followed within ten terms by a number "1" with a single sentence thereafter ending with a period.

Referring again to FIG. 16, separate begin and end tags are listed for each of types 370 and 372 indicating tags to be inserted in a record when a corresponding XML type is identified.

In addition to supporting a first XML level which corresponds to major sections of a patent specification, specification 360 also supports a second XML level which divides major patent sections into even smaller record segments. Referring still to FIG. 16 first level XMLs correspond to XMLRSs in column 364 which include a single number thereafter (e.g., XMLRS-1, XMLRS-7, etc.) while second level XMLs correspond to XMLRSs in column 364 which include two numbers thereafter. In addition, to distinguish second from first level XMLRSs, second level XMLRSs are indented to the right in column 364. With respect to second level XMLRs, the first number following an XMLRS indicates the first level XML in which the second level XML is nested and the second number indicates a specific XMLRS nested under the corresponding first XML. For example, XMLRS-5-1 is nested within XMLRS-5 which corresponding to the "Brief Description of the Drawings" and therefore further breaks down the "Brief Description of the Drawings" record segment.

In the present example, XMLRS-5-1 includes rules to identify the description of the first figure described in the description of the drawings. To this end, referring to FIGS. 16 and 19 XMLRS-5-1 requires all of the XMLRS-5 rules to be met and, in addition, requires that a paragraph begin with the phrase "FIG. 1" or some permutation thereof, end in a period or a semi-colon and be followed by a paragraph which begins with the phrase "FIG. 2" or the title "Detailed Description" or some permutation thereof. In addition, rules for identifying the end of a segment are provided. For instance, although not illustrated, XMLRS-5-1 would indicate that the FIG. 1 segment ends at the beginning of another segment at the same XML level (i.e., "FIG. 2") or a higher level (i.e., a title such as "Detailed Description").

As another example, XMLRS-7-1 is nested within XMLRS-7 which corresponds to the "claims" XML and therefore further breaks down the "claims" record segment. Similarly, XMLRS-7-2 is nested within XMLRS-7 and therefore further breaks down the "claims" record segment. In the present example XMLRS-7-1 and XMLRS-7-2 include rules to identify claims 1 and 2 of the patent specification. To this end, referring to FIGS. 16 and 20, XMLRS-7-1 requires all of the rules of XMLRS-7 to be met and, in addition, requires that a paragraph including a single sentence begin with the number "1" end with a period and that the following paragraph begin with the number "2". Similarly, XMLRS-7-2 (not illustrated in detail) requires all of the rules of XMLRS-7 to be met and, in addition, requires that a paragraph begin with the number "2", including a single sentence and that the following paragraph begin with the number "3".

Figure 21:
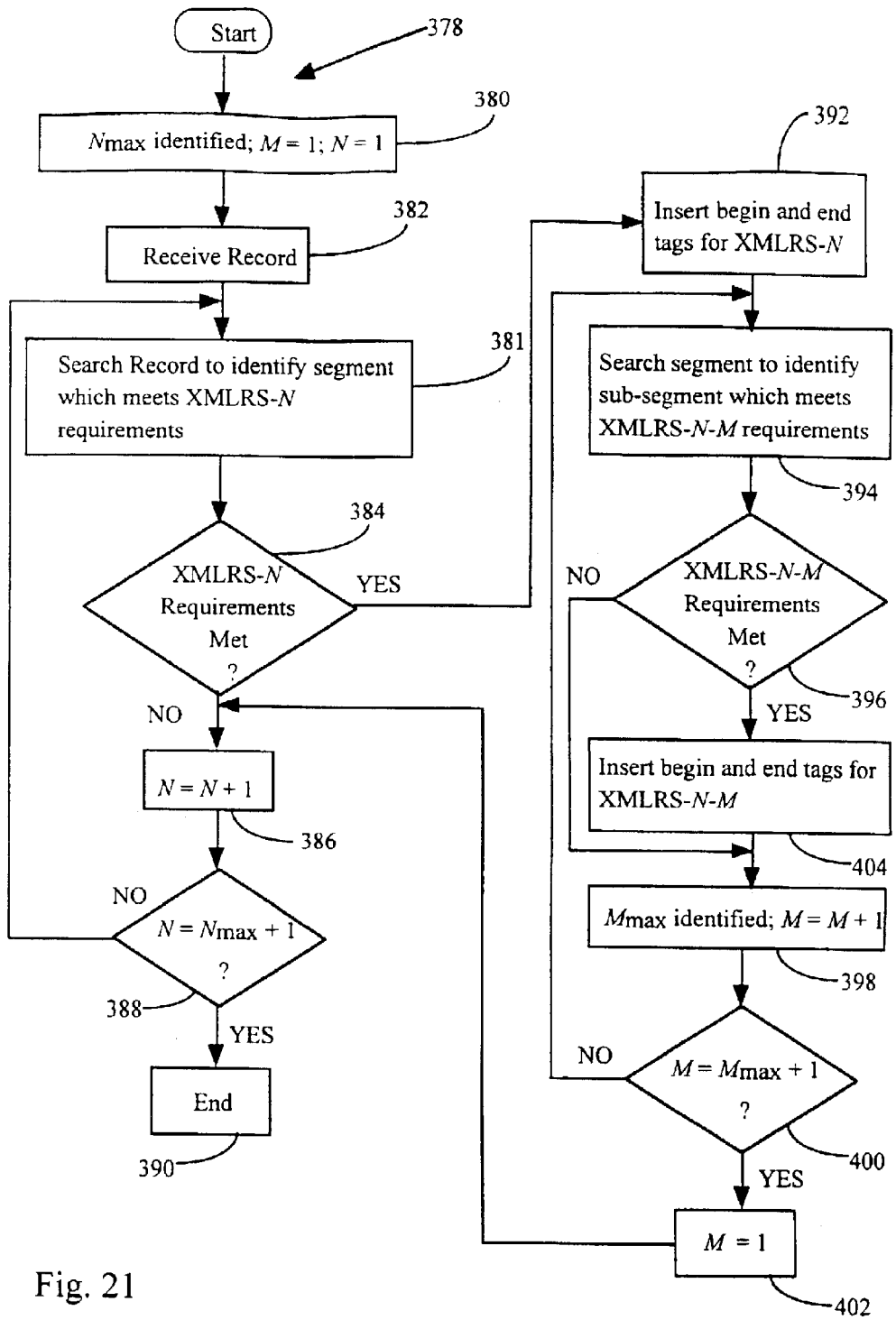
FIG. 21 is a flow chart illustrating an inventive method for supporting automatic XML tagging including nested XML tags.

Referring to FIG. 21, an exemplary XML enabling procedure 378 which supports two level XML nesting is illustrated. Referring also to FIGS. 2 and 16, initially it is assumed that processor 14 has access to XML specification 360 in database 2. At process block 380 processor 14 identifies the number N of first level XMLs in specification 360. In this case it is assumed N is 8. In addition, at block 382 processor 14 sets N and M counters equal to 1 where N represents a first level XML and M represents a second level XML.

At block 382 processor 14 receives a record. In this example the record is a patent specification and it will be assumed the specification is downloaded to processor 14 in batch form. After the record is received, at block 381 processor 14 searches the record to identify any information segments which meet the criteria specified in XMLRS-N. Here, because N is initially 1, the first rule set XMLRS-1 is used to search the record.

At decision block 384, if XMLRS-1 is not satisfied, control passes to block 386 where N is incremented by one. In the present example N is incremented to 2. At block 388 N is compared to Nmax to determine if segments corresponding to all of the XMLRSs have been sought. Where all of the segments have been sought control passes to block 390 and, to the extent possible, the record has been made XML ready. Referring still to block 388, in the present case, because Nmax is 8 and N is currently 2, control passes back up to block 381.

Referring still to FIG. 21 and specifically to block 384, where XMLRS-1 requirements are met at block 384, control passes to block 392 where begin and end XML tags associated with XMLRS-1 are inserted within the record to indicate the beginning and the end of the XML associated with XMLRS-1. Next, at block 394, processor 14 searches the segment between the XMLRS-1 begin and end tags to identify any sub-segments thereof which meet the XMLRS-N-M requirements. In this case, because N and M are both 1, the requirements searched correspond to the XMLRS-1-1 rules.

Where XMLRS-1-1 requirements are not met, at block 398 processor 14 identifies Mmax (i.e. the number of second level XMLs within first level XMLRS-1). In addition, at block 398 processor 14 increments flag M by one (i.e., in this case from 1 to 2). At block 400 processor 14 compares M to Mmax to determine if all of the XMLRS-1 second level XMLRSs have been considered. Where all of the second level XMLRSs corresponding to XMLRS-1 have not been considered, control loops back up to block 394 where processor 14 searches the segment for sub-segments which meet the criteria set out in XMLRS-1-2. Where all of the second level XMLRSs corresponding to XMLRS-1 have been considered, control passes to block 402 where M is reset to 1 prior to control passing back to block 386. At block 386 N is again incremented and hence the next XMLRS-N rule set is considered.

Continuing, referring again to block 396, where all of the XMLRS-1-1 requirements are met by a sub-segment of the segment between the XMLRS-1 begin and end tags, control passes to block 404 where processor 14 inserts the begin and end tags for XMLRS-1-1. Thereafter control passes back to block 398. The above process continues until N is equal to 9 at decision block 388 at which point control passes to block 390 and the record is, to the extent possible, XML ready.

Specifically, referring again to FIGS. 17 and 21 and block 386, when N is incremented to value 5 and control passes back to block 381, processor 14 applies the rules of XMLRS-5 to identify the description of the drawings section of the specification. When the description of the drawings is identified at block 384, control passes to block 392 and begin and end tags corresponding to the description of the drawings are inserted in the specification before and after the description of the drawings section.

Next control passes to block 394 and processor 14 searches the description of the drawings segment for a segment which meets the criteria of XMLRS-5-1 which indicates how to identify the description of the first figure described in the description of the drawings segment (see FIG. 19). Once the description of the first drawing is identified processor 14 inserts begin and end tags corresponding thereto before and after the segment at block 404. Control then passes through blocks 398 and 400 prior to being returned to block 394.

As another specific example, referring to block 384 in FIG. 21 and also to FIG. 18, when N is set equal to 7 and so that processor 14 is searching the record using XMLRS-7 to identify the claims segment of the specification, processor 14 applies the rules illustrated in FIG. 18. When the XMLRS-7 requirements are met, processor 14 inserts tags at block 392 and then searches between the tags to identify a claim 1 sub-segment at block 394 and as specified by XMLRS-7-1 (see FIG. 20). When claim 1 is identified at block 396, processor 14 inserts tags associated therewith at block 404 and returns control to block 398. Thereafter, to identify the claim 2 segment (assuming a second claim exists), processor 14 loops through blocks 398, 400, 394, 396 and 404 again.

Thus, process 378 causes processor 14 to methodically step through each XMLRS to identify record segments which meet XMLRS requirements and, when requirements are met, processor automatically inserts XML tags earmarking identified segments.

It should also be noted that while only one and two level nested XML schemes are described herein, the invention contemplates XML schemes which include many more than two levels and a processor and method which accommodate such schemes.

While one rule type is described above for determining where to place an end tag which is dependent upon the information within the segment to be indicated by the tags, another rule type depends on the location of the next start tag which is identified which is at the same or a higher tag level. For example, in the case of an exemplary patent, this rule type would require placement of an end claim 1 tag just prior to the beginning of an identified claim 2 or just prior to the beginning of some other data segment which is on the same tag level as claims (e.g., an abstract or the like).

One other aspect of the invention is that processor 14 may be equipped to, upon receiving a record, examine the record to identify information indicating which of several XML specification tables to use during the XML record readying process. To this end, it has been recognized that, even within a single facility or a single department within a facility, several different XML specifications may be required to categorize all of the information or different information types used by the processor. For example, in a medical facility there may be a first XML specification to be used with informational bulletins/brochures and there may be a second XML specification to be used to earmark information in patient examination reports. While each specification will include XMLRSs and tags which earmark specific information, the information to be earmarked may be different. For instance, the XMLRSs corresponding to a patient record may include patient ID, data, time, diagnosis, prescription, miscellaneous, etc, while the XMLRSs corresponding to brochures may include an introduction, publication date, symptoms, complications, treatments, additional contacts for follow-up, recommendations, etc.

Figure 22:
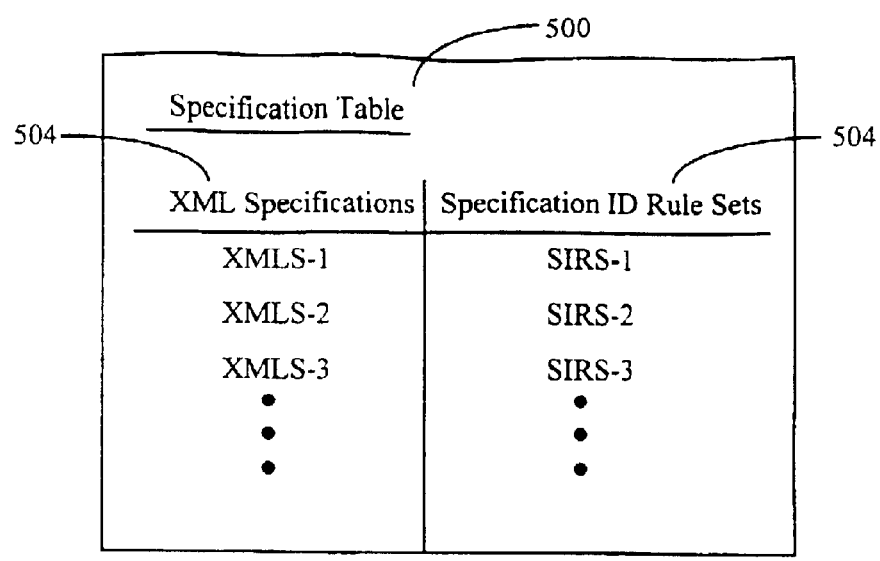
FIG. 22 is a specification table according to the present invention.

In this regard it is contemplated that, when a system supports more than one XML specification and a record is received for tag enabling (i.e., insertion of XML tags), processor 14 first examines the record to identify which XML specification to use during the tag enabling process. To accomplish this task, referring to FIGS. 2 and 22, a specification table 500 is stored on database 2. Table 500 includes a list of XML specifications supported by processor 14, table 500 including an XML specification (XMLS) list in a first column 502 and corresponding specification identification rule sets (SIRSs) in a second column 504. List 502 identifies each XMLS which is supported by processor 14. Each SIRS includes a list of rules which can be applied by processor 14 to examine a record and determine which of several different XMLSs to use during the XML readying process.

For example, in a medical facility which has had an electronic storage system for some time, it will be assumed that every patient examination record has been provided a unique record number having the form "##-######" where each "#" is a number between 0 and 9, the first two #'s correspond to the last two digits in a year (i.e., 99 indicates 1999) and the third through eighth #'s correspond to an intra-year unique examination. In addition, consistent with the specification above, each patient is assigned an ID number having the form "##XX#####" which is included on the record. While all of the records have been stored electronically it is assumed none of the records currently includes XML tags. In this case, a SIRS corresponding to an XMLS which should be used with a patient record to tag enable the record requires that the record include a record number and a patient identification number.

Referring again to FIGS. 2 and 22, when processor 14 receives a record for XML readying, processor 14 accesses SIRSs in table 500 and applies the rules therein to the record. In the present case, when the record constitutes a patient examination, by applying the SIRS rules, processor 14 recognizes that the record is a patient record and selects the XMLS corresponding thereto for XML readying purposes. Thereafter the tag enabling process described above is carried out to tag enable the record.

In the alternative, when a record is received and is to be tag enabled (i.e., tags are to be inserted), instead of having processor 14 determine which of several XML specifications to use for tag enabling, processor 14 may provide a list of possible XML specifications and enable a user, via a selection device (e.g., a mouse controlled cursor), to select one of the XML specifications. Thereafter processor 14 uses the selected specification.

Because XML and similar tag types are often hidden from a system user's view and are only identifiable via a tag enabled application so as not to obscure reading of a record, there typically is no way for a system user to observe record tags to confirm existence and correctness. To facilitate confirmation, the present invention contemplates a tag indicating feature whereby, when selected, tag indicators appear in the record. For example, in a preferred embodiment, while observing a record via a display, by selecting a specific key sequence on a keyboard, processor 14 is instructed to indicate tags within the record. For instance, patent title tags may include "<title>" and "</title>" before and after the patent title, respectively. By selecting another specific key sequence the tag revealing feature may be turned off. Other functionality may also be supported such as facilitating elimination of one, all or a subset of tags from a record via a recognizable key sequence or perhaps inclusion of additional tags via a specific key sequence.

4. Tag Modification

The present invention also contemplates that records stored on a system may be altered after tags have been added to the record and that modifications to a record may affect whether or not tags originally inserted within the record should remain or should be removed or modified. In other words, modifications including deleting, copying, altering and moving may modify the characteristics of a segment such that the segment no longer meets the requirements of the characteristic set identified in an XMLRS. For this reason the present invention also includes a processor function whereby, when a tag enabled record is modified, the modifications are monitored and, if necessary, the tags are modified to reflect record modifications.

In its simplest form, when a tag enabled is modified the inventive function includes assuming the tags are all incorrect and removing all of the XML tags from the record. To this end, referring to FIGS. 2 and 23, processor 14 monitors record modifications at blocks 420 and 422. At block 422, when the record is modified processor 14 control passes to block 424 where all record tags are removed.

While this solution is drastic, this solution ensures that tag enabled applications do not reference incorrect information. In addition, it has been recognized that in many cases complete removal of tags is required for a system to operate properly. For example, where a system supports more than one XML specification, even a single modification to a record may render all of the XML tags incorrect as the modification may cause the record to no longer meet the requirements of the XML SIRS (see FIG. 22).

Figure 23:
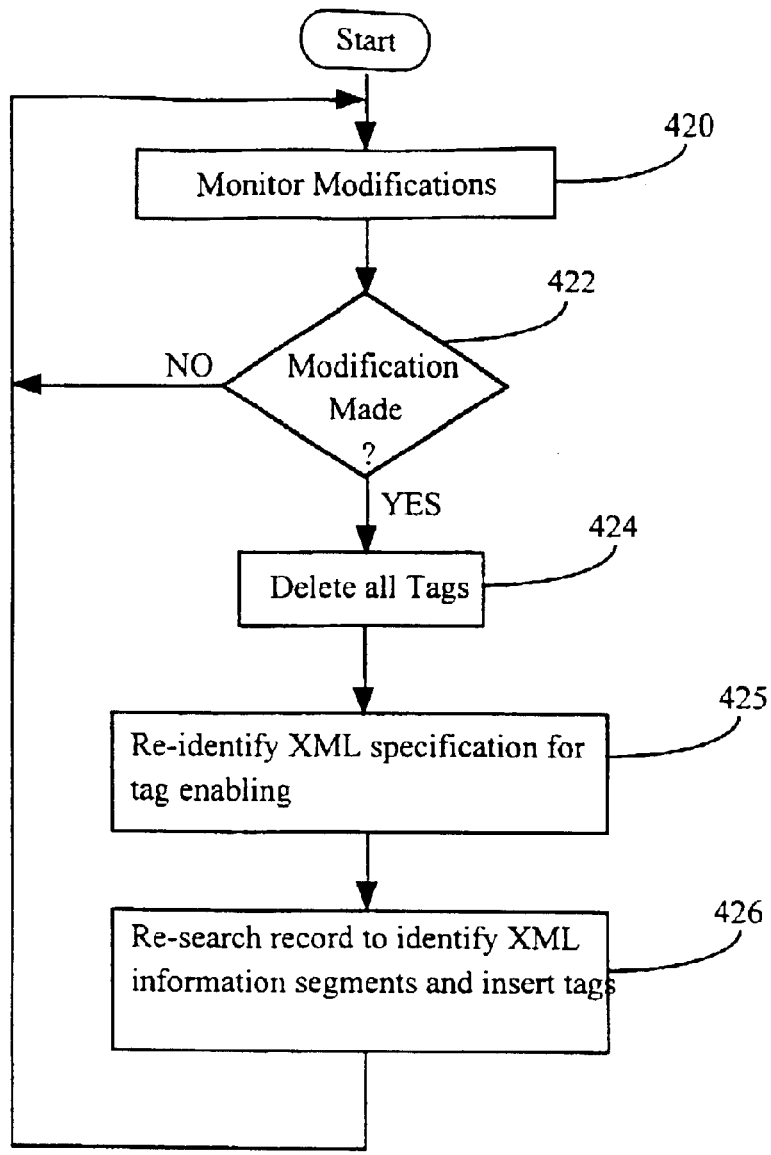
FIG. 23 is a flow chart illustrating a method for altering XML tags when a record is modified.

Referring still to FIG. 23, an extension to the simplest embodiment of this inventive feature includes the step of, after XML tags have been removed, re-identifying the XML specification to be used for tag enabling at block 425, re-searching the record as described in the preceding section of this specification to identify information corresponding to specific XMLRSs and reinserting XML tags accordingly (see block 426). This process has the advantage of again rendering an XML ready record which can be used by XML supporting applications.

According to yet another embodiment of this feature, when a segment of a tag enabled record is modified, instead of automatically removing XML tags from the entire record, tags are only removed from an "affected" portion of the record. To this end a first tag set used to earmark a first record segment and other tag sets used to earmark sub-sets of the first record segment are referred to as "related" tag sets. In addition, all tag sets which are related to a high level tag set are also said to be related. Thus, referring again to FIG. 16, the tag set corresponding to XMLRS-7 is related to each of the tag sets corresponding to XMLRS-7-1, XMLRS-7-2, XMLRS-7-3, etc., XMLRS-7-1 is related to XMLRS-7-2 and is related to XMLRS-7-3 and so on. If there were a third level of XMLRSs in FIG. 16 which was dependent from XMLRS-7 (e.g., XMLRS-7-1-1, etc.), tags corresponding thereto would be related to all other XMLRS-7 dependent tag sets.

It has been recognized that only record segments which are related to a modified segment will potentially be affected by the modification. By removing only affected tags the process of researching a record to regenerate tags is reduced appreciably.

Figure 24:
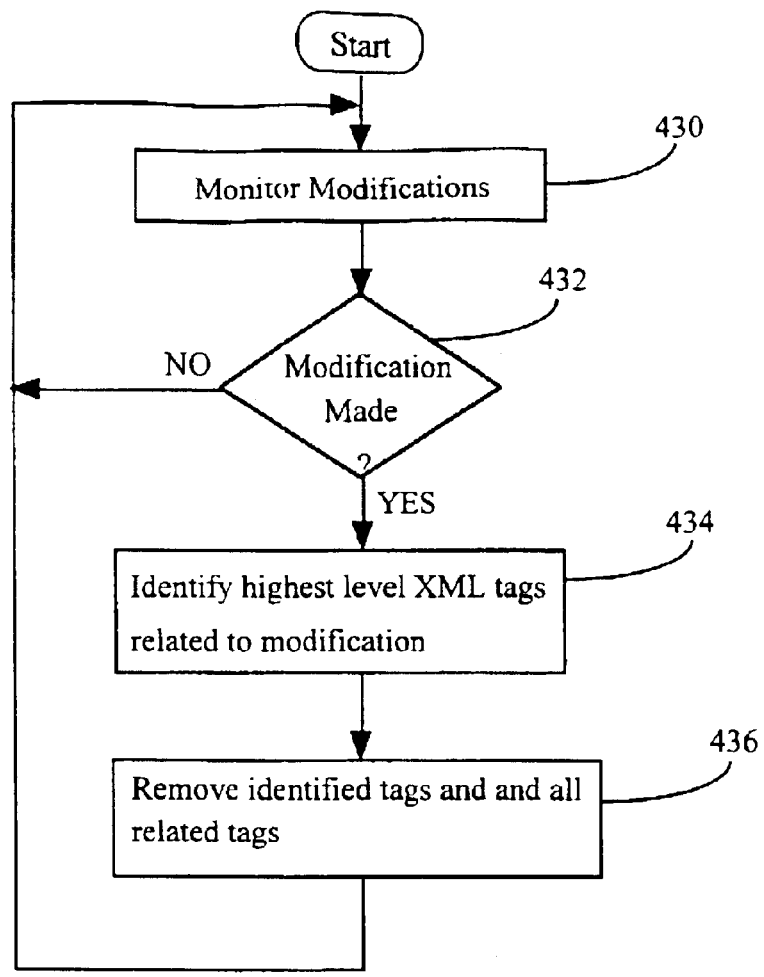
FIG. 24 is similar to FIG. 23, albeit altering the record in a different manner.

An exemplary process 429 whereby only affected tags are removed is illustrated in FIG. 24. At process blocks 430 and 432 record modification are monitored. At block 432, when a modification is identified control passes to block 434. At block 434 processor 14 identifies the highest level XML tags related to the modification. For instance, referring again to FIG. 16, where a modification occurs in a segment earmarked by tags corresponding to XMLRS-7-1 (i.e., in a first claim of a patent specification), processor 14 identifies tags corresponding to XMLRS-7 as the highest level XML tags related to the modification.

Continuing, at block 436 processor 14 removes all tags from the record which are related to the highest level tags which where identified in block 434. Referring again to FIG. 16, if tags corresponding to XMLRS-7 are the highest level tags affected by the modification, all tags associated with XMLRS-7 and XMLRS-7-Q where Q is a digit are removed at block 436. Thereafter control loops back up to process block 430 where additional modifications are monitored.

In another embodiment, when a user attempts to modify (e.g. add text, cut and paste, enter new word, merge text, etc.) a record segment which includes tags, processor 14 may prohibit the modification. In yet another embodiment processor 14 may independently consider each and every XMLRS which corresponds to record tags when a modification is made to the record to determine if the modification renders the XMLRS requirements unmet. Then, when a modified segment no longer meets requirements of one or more XMLRSs, the tags corresponding thereto may be removed.

In yet another embodiment, whenever a tag enabled application accesses a tag enabled record, prior to searching the record for required information, processor 14 automatically strips all tags out of the record, researches the record for segments consistent with the information sought by the application and inserts tags identifying the sought information. In this manner compatibility between the application and record are ensured. In addition, any modifications to the record which may have affected tag correctness are rendered meaningless.

5. Rapid Searching

As records stored on a system proliferate, the number of markup language links and tags which must be supported will grow rapidly such that searching for DRs and MRs and information segments which must be tagged will require a relatively long time. This is particularly true as more intelligence is added to the programs supported by processor 14. For example, each XMLRS DR and MMRs may have 100 or more different rules, most of which will specify, among other things, one or more terms or phrases to be located. Thus, any searching method which speeds up the process of locating a term or phrase within a record or a record segment would greatly enhance the searching, addressing and linking or searching and tagging processes described above.

To this end, the present invention includes a rapid searching method. While useful with searches for single terms, the inventive rapid searching method is particularly useful in searching for phrases or record segments which include more than one term (i.e., segments which include at least one space which separates segment terms).

Figure 28:
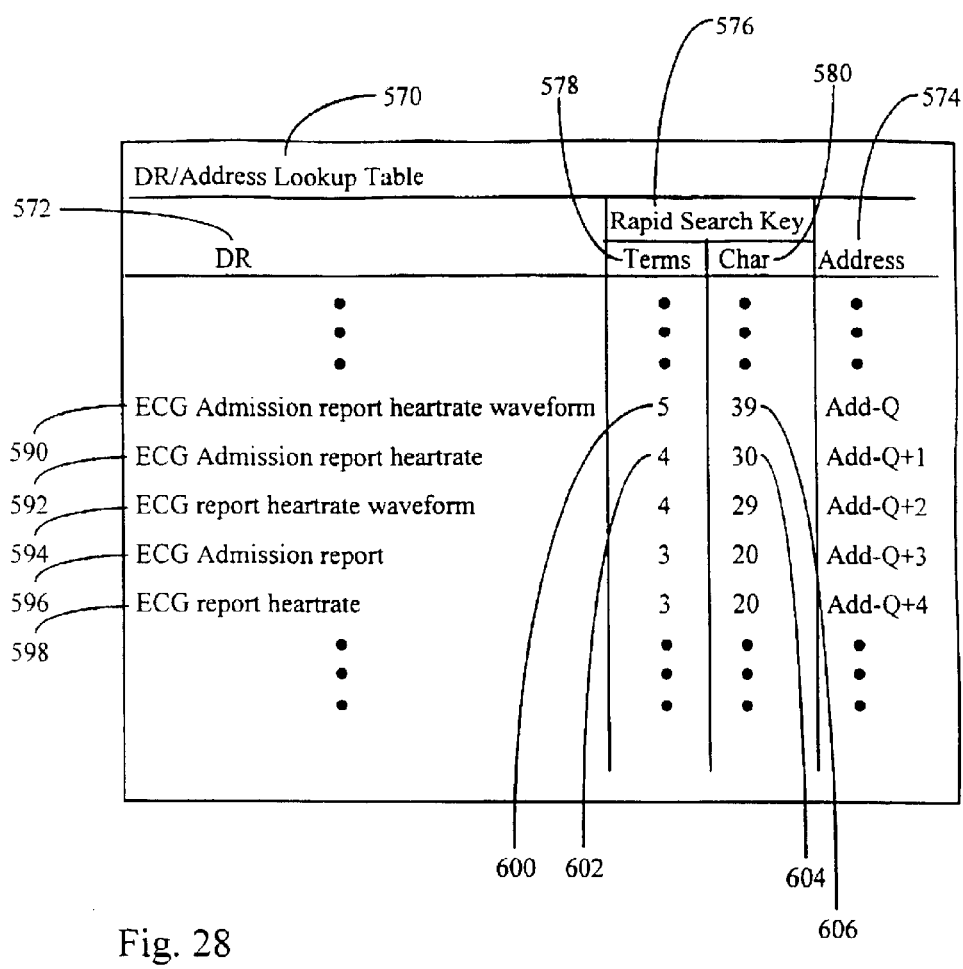
FIG. 28 is a schematic diagram illustrating a DR specification according to the present invention.

To simplify this explanation, although the rapid searching method applies to all searches wherein a term or phrase is sought, the method will be described in the context of a method for searching for DRs. Referring to FIG. 28, an exemplary DR/address lookup table 570 is illustrated which includes a DR column 572 and an address column 574. Column 572 lists all possible DRs to be sought in a record while column 574 lists a separate address for each DR in column 272. DRs in column 572 are listed alphabetically and only a small section of the DR list is illustrated. In one embodiment the alphabetical listing in column 572 is alphabetical with respect to a specific character construct within the DRs. To this end, the character construct may comprise the first characters in the DRs, the characters in a first term in each DR, or any other character construct. Exemplary DRs include "ECG admission report heart rate waveform" 590, "ECG admission report heart rate" 592, "ECG report heart rate waveform" 594, "ECG admission report" 596, "ECG report heart rate" 598, and so on.

In addition to columns 572 and 574, table 570 also includes a rapid search key column 576 which includes data corresponding to at least one and perhaps several DR length characteristics. In the present example only first and second length characteristics are included. Column 576 includes two sub-columns including a "terms" column 578 and a "characters" column 580. Each of columns 578 and 580 includes a list of numbers, a separate number corresponding to each DR in column 572. The number in column 578 indicates the number of terms in the corresponding DR referred to as a DR term count. For example, DR 590 includes five terms and hence the number 5 (i.e., 600) appears in column 578. Similarly, DR 592 includes four terms and hence the number 4 (i.e., 602) appears in column 598.

The number in column 580 indicates the number of characters in the corresponding DR and is referred to as a DR character count. For example, DR 590 includes thirty-nine characters (including spaces) and hence the number 39 (i.e., 604) appears in column 580 while DR 592 includes thirty characters and hence the number 30 (i.e., 606) appears in column 580. Key column 576 is used by processor 14 to rapidly identify DRs.

Figure 29:
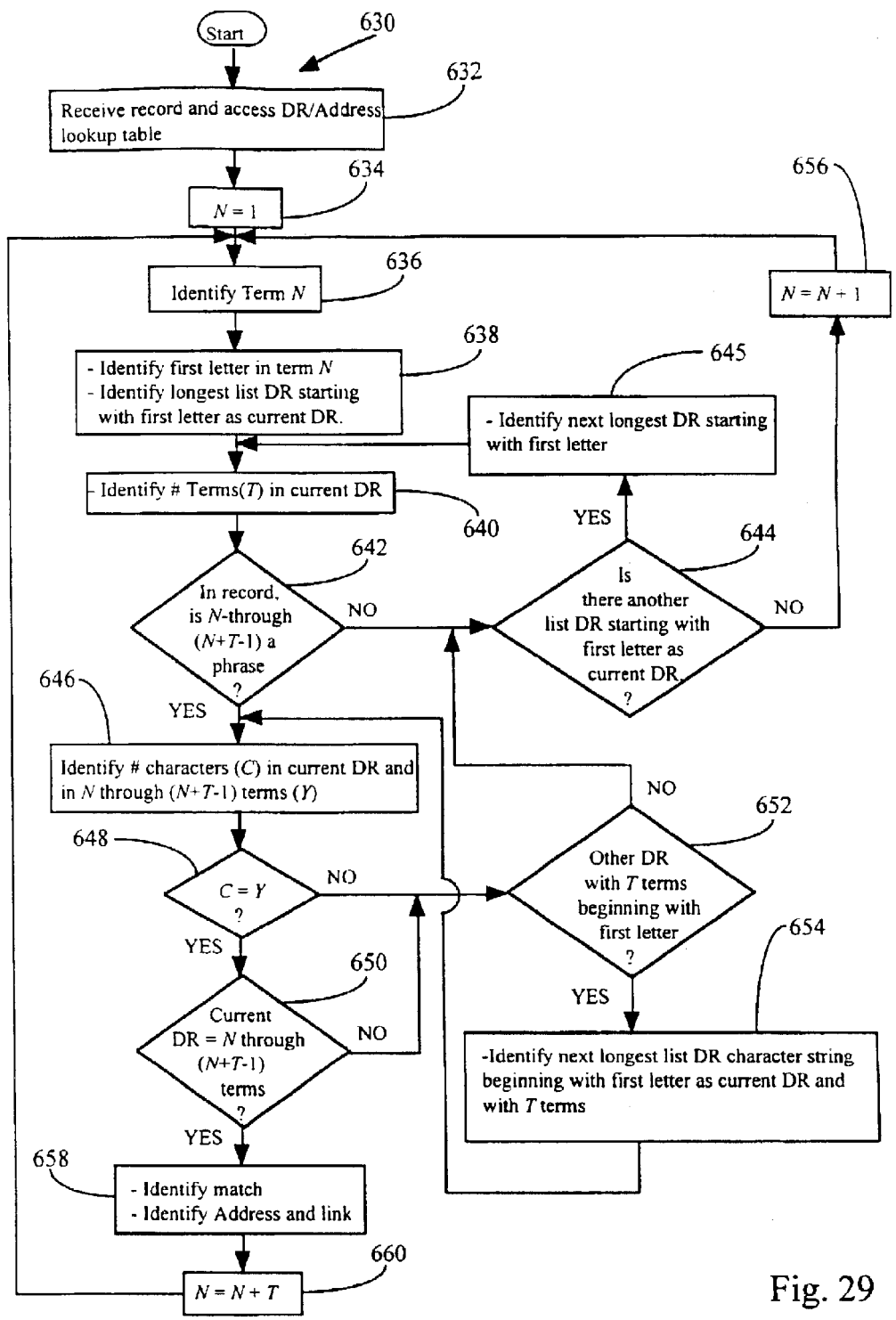
FIG. 29 is a flow chart illustrating an exemplary rapid search method according to the present invention.

An exemplary inventive searching method 630 is illustrated in FIG. 29. Referring to FIGS. 2, 28 and 29, at process block 632, processor 14 receives a record to be searched for DRs and also accesses table 570. At block 634 processor 14 sets a term indicating counter N equal to 1. Counter N indicates which term in a record which is currently considered the first term in a phrase being compared to DRs in list 570, N being incremented during method 630 until all record terms and phrases have been compared to DRs.

At block 636 processor 14 identifies term N. In the present example, because N is currently 1, processor 14 identifies the first term in the record at block 636. At block 638 processor 14 identifies the first character construct in term N. In the present example, it is assumed that the first character construct is the first character or first letter in first term N. At block 636 processor 14 also identifies the longest DR in DR column 572 which begins with the first letter. The longest DR is labeled the "current DR". To facilitate quick identification of the longest DR which begins with a letter, preferably DRs in table 570 are grouped into sub-sets wherein each sub-set includes DRs which begin with the same letter (e.g., "E"). In addition, within each sub-set, preferably, DRs are listed in an order which is related to the number of terms in the DRs. Most preferably longer DRs within a sub-set are listed prior to shorter DRs within the same sub-set.

In the present example it will be assumed that the record being examined begins with the phrase "ECG admission report information is crucial to an understanding . . .". Thus, term N is "ECG" and the first letter is "E". In addition, at block 638 the longest list DR is "ECG Admission Report heart rate waveform" (see, also 590 in FIG. 28) and is labeled the current DR.

Continuing at block 640 processor 14 identifies the number of terms (T) in current DR 590 as five (i.e., see 600 in FIG. 28) which is referred to as a "first value". Next, at decision block 642 processor 14 determines whether or not terms N through (N+T−1) (i.e., a current segment) corresponds to a complete phrase within the record. For example, assume the record includes the segment " . . . in the ECG report. In addition one has to . . . ". In this case, the four terms which follow term "ECG" are separated by a period and hence form two separate phrases. In this case, control passes to block 644. In the present case, however, in exemplary phrase "ECG admission report information is crucial to an understanding . . . ", terms N (i.e., "ECG") through N+T−1 (i.e., "is") are part of a single phrase and control passes to block 646.

At block 646 processor 14 uses table 570, and specifically column 580, to determine the number of characters (C) (also referred to as a "second value") in the current DR. Column 580 indicates 39 characters and hence second value C=39. In addition, at block 646 processor 14 counts the number of characters (including spaces) which form the phrase which constitutes N through N+T−1 terms. In the exemplary phrase between the first letter of term "ECG" and the last letter of term "is", the N through N+T−1 phrase includes 35 characters and hence Y=35.

At decision block 648 character counts C and Y are compared. Where DR second value C is equal to record character count Y, control passes to decision block 650 which is explained in more detail below. In the alternative, control passes to decision block 652. In the present example, counts C (i.e., 39) and Y (i.e., 35) are not equal and hence control passes to block 652. At block 652 processor 14 determines if there are other DRs in list 570 which include T (i.e., 5) terms which begin with the first letter E. If another DR with 5 terms beginning with letter E exists control passes to block 654 where the other DR with 5 terms beginning with E is selected as the current DR and control passes back to block 640 where the process continues with the new current DR.

In the present case, however, at block 652 there are no other DRs with 5 terms which begin with letter "E" and therefore control passes to block 644. Whenever control passes to block 644 processor 14 determines if there is another DR in table 570 which begins with the first letter and has less than T terms. In the present example, if table 570 does not include another DR beginning with "E" which includes less then T terms, control passes to block 656 where N is incremented by one and then passes back to block 636 where a new first phrase term (i.e., the N+1 term) is selected for DR comparison.

In the present example, referring to FIG. 28, there are several DRs which begin with "E" and have less than five terms and therefore control passes from block 644 to block 645 where the next longest DR starting with letter "E" is selected for DR comparison. Control then passes to block 640. In the present case, the next longest DR beginning with "E" is "ECG admission report heart rate" 592.

Control loops through blocks 640, 642, 646, 648, 652, 654, 644 and 645 several more times until, at block 645, processor 14 identifies DR "ECG Admission Report" 596 (see, FIG. 28). At that point, processes 14 steps through blocks 640 and 642 and control passes to block 646 where DR character count C is identified as 20 and the record phrase character count Y is also identified as 20. Thus, at block 648 counts C and Y are equal and control passes to block 650. At block 650 the current DR and the phrase comprising terms N through N+T−1 are compared. Where the current DR and compared phrase are not identical control again passes to block 652. However, where the DR and compared phrase are identical control passes to block 658 where processor 14 recognizes a DR record phrase match, looks up the corresponding address in table 570 and forms a link. In the present example, DR 596 matches record phrase "ECG Admission Report" and hence address ADD−Q+3 is used to link the DR to the record at address ADD−Q+3.

At block 660 N is incremented by T. in the present example T, the number of terms in the most recent current DR, is 3 and therefore N is incremented to 4 (i.e., 1+3=4). Control then loops back up to block 636 where, in this case, processor 14 identifies the 4th term "information" (i.e., the record began "ECG admission report information is critical to an understanding" and hence the 4th term is "information").

This process of searching and linking continues until all record text has been searched and links formed.

It should be understood that the methods and apparatuses described above are only exemplary and do not limit the scope of the invention, and that various modifications could be made by those skilled in the art that would fall under the scope of the invention. For example, while the invention is generally described in the context of HTML linking and XML tags and rule sets, clearly other linking and tagging systems are contemplated and the invention should not be so limited. In addition, both HTML and XML features described above may be included in a single system to achieve synergistic advantages. In addition, as indicated above, while some preferred resolution rules are described, the invention is not meant to be so limited in its broadest form and generally includes any rule set and processor which applies the set where the rules eliminate ambiguity between DRs and DR/MR combinations.

Moreover, while the exemplary rapid search feature described above includes first and second DR length characteristics (i.e., number of terms and number of characters), other embodiments may include only a single length characteristic or may include many other length characteristics which are examined prior to text comparison. For example, another length characteristic which may be used might be the number of characters in a first term in a record phrase which is compared to the number of characters in the first term of a DR. The important aspect of the rapid search feature is that DRs include characteristics in addition to their characters which can be sought to narrow the possible DRs to a small number prior to character comparison and that searching for such additional characteristics is much more rapid than a full fledged character search. In other words, each search time is decreased appreciably by performing a rapid DR search based on DR length characteristics to narrow the possible DR list and then performing a detailed character search to identify a specific DR from the narrow list of possible DRs.

Furthermore, the rapid search method may be employed on a single phrase (as opposed to an entire record) or may include a DR list which is not alphabetized or using a single DR as opposed to a DR list or, may require a processor to identify DR length characteristics prior to comparison instead of relying on a table key.

Moreover, after an SR is associated with a record or record segment, the inventive system may also monitor modifications to the record and, when a modification would alter the correctness of the SR-record association the system may be programmed to change the association through eliminating the association, re-identifying if another suitable SR-record association exists and creating any suitable SR-record association.

6. Tag Verification Prior to Performance of Tag Related Action

As described above in the section of this specification entitled "Tag Modification", the invention contemplates that records can be altered or modified after tags have been automatically (e.g., via batch processing) added or inserted into the record. When a record is modified after tags have been added to the record, prior to using the tags to perform actions, the tags should be examined to determine whether or not the tags remain accurate. Where the tags no longer remain accurate the tags should at the very least be removed so that they cannot be used subsequently to perform an unintended action. In addition, where tags are removed, in at least some cases a new analysis may be performed to determine if new tags should be added to the record.

In one embodiment record segments are monitored as they are modified, and when a modification is made any tags previously automatically inserted related to the record or record segment are verified as described above to determine if they should remain, be modified, or be removed. Similarly, when text prior to and/or following the tagged record segment is modified, the modifications to the preceding and following text, may also be analyzed as those modifications may cause the tagged segment to be inaccurately tagged. The text that includes the tagged record segment and text prior to/and or following the record segment is referred to as the record segment area. The phrase "record segment area" is also useable to refer to just the tagged record segment.

Immediate verification of tag accuracy may not always be desired either for inserting tags based on record segment characteristics or for modifying or removing tags. To this end, some systems may allow a user to select a batch code processing feature (e.g. by selecting an icon or menu choice entry) that adds tags and/or codes to a record or document during a batch processing exercise based on record segment characteristics. Unfortunately, where batch processing is used to automatically add tags/codes to a record based on record content or some other information related to the record and the content or other information used to characterize the tagged or coded record segment is altered, the automatically inserted tags may be erroneous and could lead to unexpected and erroneous actions. In this case erroneous actions may be avoided if the batch process is re-run on the modified record. However, where a system user inadvertently forgets to re-run the batch process erroneous actions will inevitably result. For instance, in the context of a medical facility incorrect patient records may be retrieved if erroneous hyperlink tags/codes are left in a modified document. Similarly, erroneous record segments may be retrieved where incorrect XML tags are not removed from a modified record.

Herein the term "action" should be interpreted broadly to include but not be limited to activating a hyperlink to retrieve data, activating a record segment to retrieve data, storing a record at a computer system or database address, using inserted tags to provide information to a database, providing tags or tagged information to another program, etc.

To prevent unintended and misleading actions based on inaccurate codes and tags, one aspect of the present invention monitors records including tags and codes for modifications. In at least one embodiment of the invention a modification flag is set that indicates when a record has been modified. After record tags and codes are verified, the modification flag is reset until another modification is identified. Verification may require an affirmative request from a user to verify or, in the alternative, may be automatic whenever some "verify event" occurs. For instance, a verify event may include a user causing a processor to access or read a record from a database and display the record on an interface display for review. Other verify events may include storing a record or a segment of a record, e-mailing a record or a segment, copying or pasting a record segment, attempting to use a record segment to perform some action (e.g., selection of a hyperlink phrase, an attempt to obtain an XML tagged record segment, etc.), etc.

One other type of verify event may include simply moving an editing cursor away from a specific record segment or a sub-set of segment including content that may be useable to characterize the specific record segment. For instance, where a first record segment is characterized by characteristics that match characteristics associated with a first record code or tag, an initial batch process will insert a first record code into the record to earmark the record segment. When a system user alters the first segment, the first record code associated with the record segment may not be verified until an edit cursor is removed from the first segment—a verify event (e.g., placed in another record segment or in another window opened on a system user's desktop). After the cursor is moved from the first segment the verification process may be commenced for the first segment.

Where verification is delayed until after a verify event occurs, while codes that may be rendered inaccurate by record modifications may not be deleted, those codes may nevertheless be rendered unactionable to avoid actions based on potentially inaccurate tags/codes. For instance, assume the verify event is a store command to store a modified record. During record modifications a system user may cause certain modifications that could render tags/codes inaccurate such as altering text immediately before or after a hyperlink phrase. Here, according to this aspect of the invention, the hyperlink text and related address may be left visibly unchanged but the link would be disabled until after verification is complete. This feature reduces user distractions related to a on the fly code modifications yet avoids erroneous activities.

In some cases there may be several different record segments (i.e., a segment sub-set) that include information used by the batch processing protocol to characterize a first record segment and identify tags therefore. For instance, in the case of a medical record including thirty fields, two fields may include a patient ID number and a date, each of which may be used to identify tags and codes corresponding to other record segments. Hereinafter, all record segments that include content that may be used to characterize another segment for code or tag identifying purposes will be referred to as a related sub-set. Here, in some embodiments verification may not be commenced until the cursor is removed from all related sub-set segments. Thus, where a related sub-set includes four separate segments, after at least one of the four segments is modified, re-verification would not commence until the cursor is moved into a record segment that is not included in the related sub-set.

Other verify events may require a user to enter a particular character or a specific series of characters. For instance, a space, specific punctuation (e.g., a closed bracket, a semi-colon, two periods, etc.), etc. may signify a verify event. In some cases the end of a sentence (e.g., a period followed by two spaces) or a paragraph (e.g., a carriage return, line feed, new page mark, etc.) may comprise a verify event.

In another embodiment the processor may be programmed to wait until a cursor is removed from a segment or related sub-set of segments prior to attempting to identify segment modifications. After the cursor is removed from the related sub-set, if at least one segment modification was made, in some embodiments all codes will be removed from the specific segment without further inquiry. In other embodiments, where at least one modification was made, the processor may perform an algorithm to determine if the modification(s) affect the tags/codes and will only remove incorrect tags/codes. In still other embodiments where at least one modification was made all codes in the specific segment are removed and the processor automatically re-batch processes the specific segment to insert new tag/codes where appropriate.

In at least some embodiments of the invention any tags or codes that are added to a record by a user prior to a batch code and tag process being performed may be left intact and may not be verified. Where re-verification (e.g., batch processing after record modifications) is to occur, in some cases an advisory message may be provided (e.g., displayed) to a system user indicating that a record is being batch processed and perhaps allowing the user to stop the processing if desired. Thus, for instance, after codes have been added to a record and once at least one record modification occurs, when a verify event (e.g., a record store command) occurs, the system may allow a user to either authorize verification or forego authorization.

In some embodiments a record may be divided into record sections or segments (e.g.; paragraphs, sentences, etc.) and a separate flag may be used to determine if a section modification has been performed subsequent to the most recent verification process being performed. By using multiple flags to earmark modified record sections the analysis step can be limited to analysis of the modified sections only.

In some cases an entire document will have to be analyzed when a record is modified. For example, when a DR is separated from a MR by a paragraph or more it may be necessary to examine all of the text and other information associated with a record to determine if tags and codes remain correct after record modifications. Here, the document or the document section modified will be analyzed for all appropriate tags to be added to a document and the batch verification process is not limited to the text that had previously been tagged.

In each of the above cases any tags or codes automatically (i.e., not manually inserted by a system user) inserted in the record are verified prior to any action that is performed utilizing the tags, even though the tags may not be verified immediately as they are entered.

In some cases when a record is analyzed a conflict will be identified between tags that are to be inserted via an automatic batch process into the record and tags that are already present in the record (e.g. inserted by a user or provided in a record by another program). Instead of inserting new tags in error or against the standard formatting requirements for such tags (e.g. XML tag hierarchy), it is contemplated that an advisory message may be displayed or provided to a system user indicating the potential conflict. In addition, the system may automatically provide an option for the system user to either maintain the existing tags and codes in the record and forego generating the automatic batch coding and tagging or to eliminate the existing tags and codes and perform the batch coding process. In other embodiments, where batch tags and existing tags conflict the system may automatically eliminate the existing tags and insert the batch generated tags.

It should be noted that while the verification aspect of the present invention has been described in the context of XML tags and other markup language tags, it is contemplated that the present invention will work with any types of record code (including markup language tags) that can be inserted into a record or associated with a record segment (e.g., when a record code is maintained in a separate list) by analyzing record segments to determine if the segments correspond to a characteristic set associated with the record code. Previously described tags can be considered to be record codes.

It is also contemplated that when a record segment corresponds to a DR and a data retrieval address is formatted to access or retrieve the referenced record, the address can also be verified by using the address to determine that a record has been stored at that address. When a record has not been stored at the address the DR can be ignored and no tags inserted into the record related to the DR or an advisory message identifying the missing referenced record can be presented to the user allowing the user to accept the insertion of the corresponding tag(s) or not.

Figure 30:
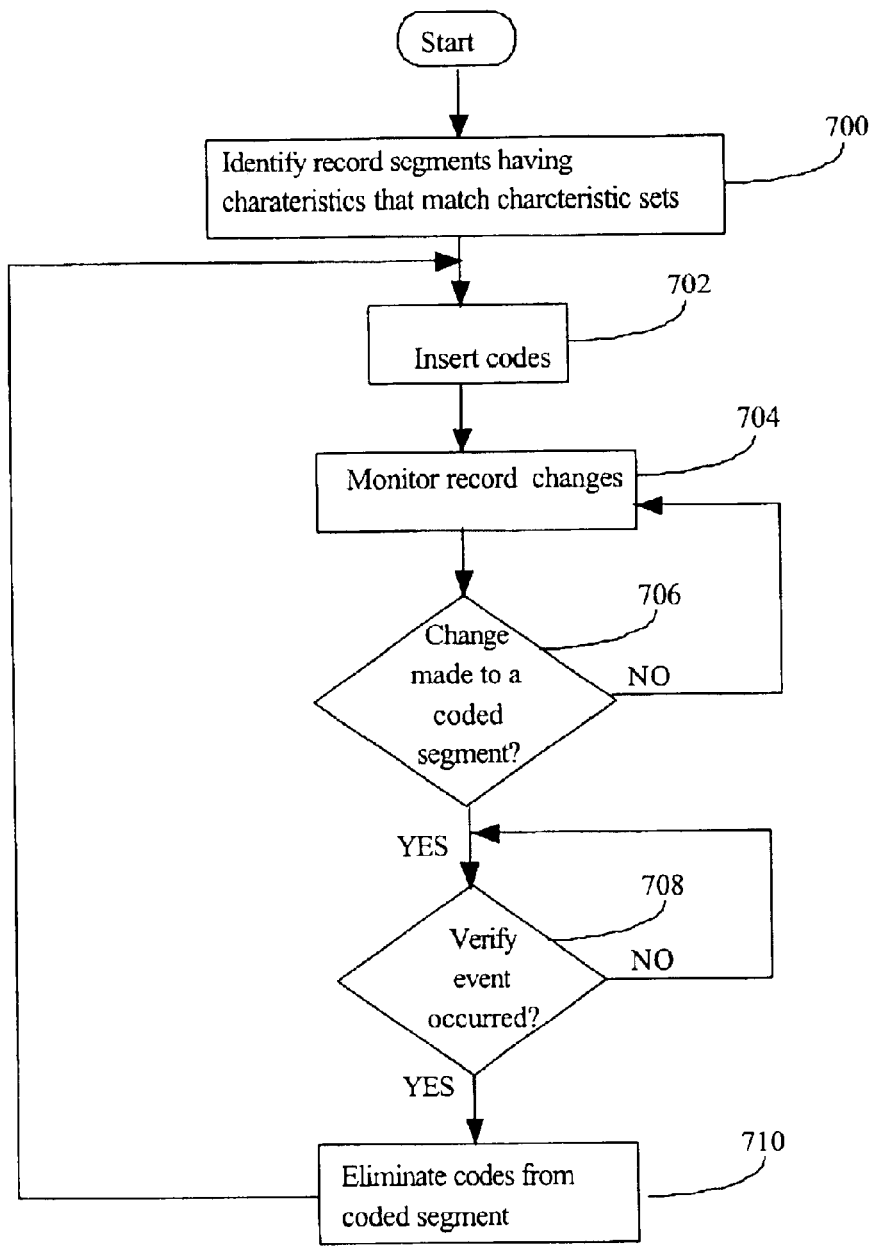
FIG. 30 is a flow chart illustrating an exemplary verification method according to the present invention.

Referring now to FIG. 30, one exemplary verification method according to the present invention is illustrated. In FIG. 30, at block 700, a processor identifies record segments having characteristics that match a characteristic set associated with a particular record code. For example, rules for inserting XML tags like the rules described above may comprise the characteristic sets. At block 702 record codes associated with specific characteristic sets are inserted into the record to earmark record segments that have characteristics that match the characteristic sets. At block 704, after the batch processing has been performed to insert codes into the record, the record is monitored for any type of modification or change. At block 706, where no record modifications are made, control simply loops back up block 704 where the monitoring process continues. Eventually, when the record is modified by, for instance, adding text, deleting text, etc., control passes from block 706 to block 708. At block 708 the processor monitors system operation to identify when a verify event occurs. Here it will be assumed that the verify event comprises movement of an editing cursor away from the coded record segment that has been modified.

Until a verify event occurs (e.g., the cursor is moved away from the modified coded segment), even when additional changes are being made to the coded record segment which has already been modified, processor control loops back through block 708 monitoring for occurrence of a verify event. After a verify event occurs, control passes from block 708 to block 710 where codes within the particular record segment are eliminated after which control passes back up to block 700 once again.

According to this embodiment of the invention, after codes are eliminated at block 710, the automated batch process corresponding to block 700 and 702 is again repeated to determine whether or not new tags should be added to the record. After new tags are added to the record the record is again monitored for additional changes and the process is repeated.

Figure 31:
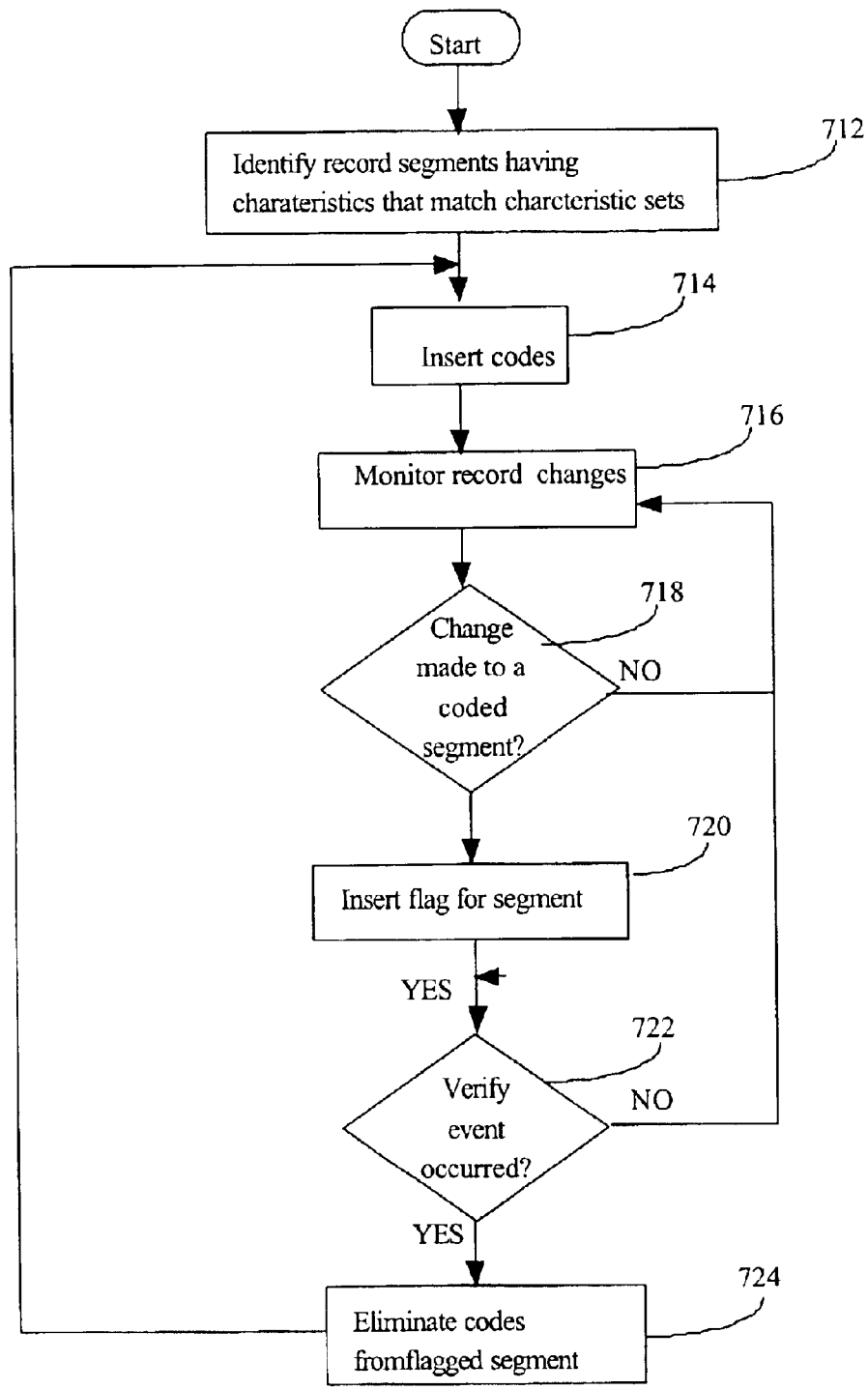
FIG. 31 is similar to FIG. 30, albeit illustrating a second verification method according to the present invention.

Referring now to FIG. 31, another verification method according to the present invention is illustrated. In FIG. 31, blocks 712 and 714 are similar to blocks 700 and 702 in FIG. 30 and therefore will not be described here in detail. It should suffice to say here that blocks 712 and 714 correspond to or comprise an automated batch processing system whereby tags and/or codes are added to a record to distinguish various record segments from each other. Continuing, at block 716, a processor monitors a record including tags and codes for any record changes. At block 718, where record changes are not made, control loops back up through block 716. However, at block 718, where a change is made to a coded record segment, control passes to block 720 where a flag is used to earmark the record segment that has been modified.

Next, at block 722, the processor again monitors to determine whether or not a verify event occurs. In this example, it will be assumed that a "save" command to save the modified record comprises a verify event. Where a verify event does not occur, control passes back up to block 716 where the processor continues to monitor for additional record changes. Blocks 716, 178 and 720 cooperate to earmark additional record segments with modify flags indicating that the segments have been modified. This process continues until a verify event (e.g., save command occurs at block 722).

After a verify event occurs at block 722, control passes from block 722 to block 724 where tags within the flagged record segments are eliminated. For example, where five different coded segments have been modified during an edit process, step 720 earmarks each of the five separate segments with a segment specific flag and, therefore, at block 724, tags are eliminated from all five of the flagged segments. After block 724 control again passes back up to block 712 where the automated batch tagging and coding process is repeated to insert new and correct tags into the entire record including the five segments from which tags were removed.

To apprise the public of the scope of this invention, the following claims are made:

What is claimed is:

1. A method to be used with a processor capable of facilitating at least a sub-set of possible records modifications including copying, moving, altering and deleting, the processor having access to information characteristic sets that correspond to records codes that can be inserted into records to identify record segments and that can be used to perform actions, the method for automatically inserting record codes into records and for verifying record codes prior to performing actions based thereon, the method comprising the steps of:

specifying at least one verify event that will occur between a time a record is modified and a time an action based on record codes is completed;

creating a first record;

identifying record segments in the first record that have segment characteristics that match at least one of the characteristic sets;

inserting record codes into the first record to distinguish the record segments having segment characteristics that match the characteristic sets from the other segment in the first record;

monitoring for a verify event; and when a verify event occurs, verifying accuracy of the record codes in the first record.

2. The method of claim 1 wherein the step of verifying includes determining if first record modifications have occurred and where first record modifications have occurred, determining if the modifications cause additional record segments in the first record to have segment characteristics that match at least one of the characteristic sets and inserting record codes into the first record to distinguish the additional record segments having segment characteristics that match the characteristic sets from the other segments in the first record.

3. The method of claim 1 wherein the step of verifying includes determining if first record modifications have occurred and where first record modifications have occurred, determining if the modifications distinguish the segment characteristics of the segments distinguished by the inserted record codes from the corresponding characteristic sets and, where the modifications distinguish segment characteristics of a segment distinguished by inserted record codes from the corresponding characteristic set, eliminating the record code.

4. The method of claim 3 wherein the step of verifying further includes the steps of, if a record code is eliminated, after eliminating the record code, determining if the characteristics of any segment of the document match one of the characteristic sets and, if a segment matches one of the characteristic sets, inserting record codes corresponding to the matching characteristic set into the first record to distinguish the matching segment from other record segments.

5. The method of claim 1 wherein the step of verifying includes identifying first record modifications and, when a modification occurs, determining if the modification could possibly distinguish segment characteristics of any of the coded segments from the corresponding characteristic sets and, if the modification could possibly distinguish a segment, eliminating the record codes associated with the segment.

6. The method of claim 5 wherein the step of verifying further includes the steps of monitoring the record for modifications and, when a modification occurs, identifying all record segments that have characteristics that may be altered by the modification and eliminating all of the record codes associated with the identified record segments.

7. The method of claim 5 wherein the step of verifying further includes the steps of, if a record code is eliminated, after eliminating the record code, determining if the characteristics of any segment of the document match one of the characteristic sets and, if a segment matches one of the characteristic sets, inserting record codes corresponding to the matching characteristic set into the first record to distinguish the matching segment from other record segments.

8. The method of claim 1 wherein the step of verifying includes the steps of receiving the first record, eliminating all existing record codes, using the characteristic sets to identify record segments having characteristics that match the characteristic sets and inserting record codes into the first record.

9. The method of claim 8 wherein at least one verify event includes accessing the first record.

10. The method of claim 8 wherein at least one verify event includes storing the first record for subsequent use.

11. The method of claim 1 wherein one segment distinguished by a first record code is a first record segment having first segment characteristics that may be related to a related sub-set of first record segments and wherein the step of verifying includes monitoring the related sub-set for modifications and, when at least one related sub-set modification occurs, eliminating the first record code from the first record.

12. The method of claim 11 further including the step of, after any related sub-set modification has occurred and prior to a verify event, rendering the first record code corresponding to the first record segment unactionable.

13. The method of claim 11 for use with an interface that enables a system user to move a cursor about a display within the first record and wherein at least one verify event includes movement of the cursor from the related sub-set.

14. The method of claim 5 wherein the step of determining if the modification could possibly distinguish segment characteristics of any of the coded segments from the corresponding characteristic sets includes, for each code record segment, monitoring modifications to a related record portion selected from the group consisting of the record segment, a paragraph containing the record segment, a sentence containing the record segment, and a record segment area including the record segment.

15. The method of claim 1 wherein the record codes include at least one hyperlink code linking first record segments to second records, formatting code indicating that the first record segments are associated with second records, XML codes, access codes to second records, address formatting codes associated with second records and formatting address codes for the first record.

16. The method of claim 1, where actions based on record codes include at least one of activating a hyperlink related to a first record code to retrieve a second record, activating a database link related to a first record code to retrieve a second record, sending at least the a section of the first record including a record segment to a computer address, copying at least a section of the first record including a record section, inserting at least a section of the first record into a second record, saving the first record to a storage device and accessing at least a section of the first record form within a second record.

17. The method of claim 1 where each code includes a code pair including a start code and an end code, the step of inserting including placing the start code before a record segment and the end code after a record segment.

18. The method of claim 3 further including the steps of, prior to eliminating a record code, indicating that the first record has been modified and allowing a system user to determine if the record code should be eliminated.

19. The method of claim 1 wherein at least one verify event includes receiving a action command requiring an action to be performed that is associated with the first record.

20. The method of claim 1 wherein at least one verify event includes receiving an action command requiring an action to be performed that is associated with at least one of the coded record segments.

21. The method of claim 20 wherein the step of verifying includes, if the coded record segment associated with the required action has characteristics that are different than the characteristic set associated with record code, indicating a mismatch to a system user.

22. The method of claim 1 further including the steps of, prior to a verify event and after record codes have been inserted into the first record, monitoring the first record for modifications and, when a modification occurs, flagging the first record as modified.

23. The method of claim 22 wherein the step of verifying further includes removing all codes from the first record, determining if the characteristics of any first record segment match one of the characteristic sets and, if the characteristics of a segment match one of the characteristic sets, inserting record codes corresponding to the matching characteristic set into the first record to distinguish the matching segment from other record segments.

24. The method of claim 1 further including the steps of, after inserting the record codes into the first record and prior to a verify event, monitoring the first record for modifications, identifying all record segments including record codes that may be rendered inaccurate because of the modifications performed and flagging all of the record segments including record codes that may be inaccurate.

25. The method of claim 24 wherein the step of verifying includes eliminating all inaccurate record code in the flagged segments.

26. The method of claim 25 wherein the step of verifying further includes examining the first record to identify additional record codes that should be added to first record as a function of the record content and adding the identified record codes to the first record.

27. The method of claim 25 wherein the step of eliminating includes eliminating all record codes from the flagged record segments.

28. The method of claim 1 wherein a processor performs the steps of identifying and inserting, the first record includes at least some manually inserted codes and the step of verifying includes verifying only processor inserted codes prior to allowing actions related thereto to be performed.

29. The method of claim 28 further including the step of determining when verification will cause processor inserted codes to conflict with manually inserted codes and, when a conflict exists, providing a choice to a system user of accepting one of the processor inserted codes and the manual codes.

30. The method of claim 1 wherein at least one verify event includes at least one of accessing any part of the first record, storing any part of the first record, copying any part the first record, attaching any part of the first record to another record, commanding that an action be performed that is related to the first record and indicating that edits to any part of the first record have been completed.

31. A method to be used with a processor capable of facilitating at least a sub-set of possible record modifications including copying, moving, altering and deleting, the processor having access to information characteristic sets that correspond to record codes that can be inserted into records to identify record segments and that can be used to perform actions, the method for automatically inserting record codes into records and for verifying record codes prior to performing actions based thereon, the method comprising the steps of:

specifying at least one verify event that will occur between a time a record is modified and a time an action based on record codes is completed;

creating a first record;

identifying record segments in the first record that have segment characteristics that match at least one of the characteristic sets;

inserting record codes into the first record to distinguish the record segments having segment characteristics that match the characteristic sets from the other segments in the first record;

monitoring for modifications to the first record;

where the first record is modified, monitoring for a verify event; and when a verify event occurs, verifying accuracy of the record codes in the first record.

32. The method of claim 31 wherein the step of monitoring for modifications includes identifying record segments having characteristic sets that may be altered by the modifications and wherein the step of verifying includes verifying the record codes associated with the record segments having characteristic sets that may have been altered by the modifications.

33. The method of claim 32 wherein the step of verifying includes eliminating the record codes from the record segments having characteristic sets that may have been altered by the modifications.

34. The method of claim 33 wherein the step of verifying further includes the steps of, if a record code is eliminated, after eliminating the record code, determining if the characteristics of any segment of the document match one of the characteristic sets and, if a segment matches one of the characteristic sets, inserting record codes corresponding to the matching characteristic set into the first record to distinguish the matching segment from other record segments.

35. The method of claim 31 wherein at least one verify event includes at least one of accessing any part of the first record, storing any part of the first record, copying any part the first record, attaching any part of the first record to another record, commanding that an action be performed that is related to the first record and indicating that edits to any part of the first record have been completed.

36. A method to be used with a processor and at least a first record, the processor capable of facilitating at least a sub-set of possible record modifications including copying, moving, altering and deleting, the processor linked to characteristic sets which correspond to record codes, at least a first sub-set of first record segments having characteristics that can be used to distinguish a first record segment from other record segments, the first record also including a first record code which can be used by the processor and other processors to distinguish the first segment from other record segments, at least one processor performing at least one action based on the record codes in the first record, the method for verifying record codes prior to actions based thereon, the method comprising of:

monitoring the first segment sub-set for modifications and, when at least one first segment sub-set modification occurs, eliminating the first record code from the first segment sub-set prior to allowing an action related to the first record code to be performed.

37. The method of claim 36 wherein the step of monitoring the first segment sub-set for modifications includes waiting for a verify event to occur and, when a verify event occurs, identifying any first segment sub-set modifications.

38. The method of claim 37 further including the step of, after any first sub-set modification has occurred and prior to the verify event, rendering the first record code corresponding to the first record segment unactionable.

39. The method of claim 37 for use with an interface that enables a system user to move a cursor about a display within the first record and wherein the step of waiting for a verify event includes monitoring when the cursor is removed from the first segment sub-set.

40. The method of claim 36 wherein there are additional characteristic sets which correspond to additional record codes and, wherein the step of verifying further includes the steps of, if the first record code corresponding to the first characteristic set is eliminated, after eliminating the first record code, determining if the characteristic of any segment of the document match one of the characteristic sets and, if a segment matches one of the characteristic sets, inserting record codes corresponding to the matching characteristic set into the first record to distinguish the matching segment from other record segments.

* * * * *

UNITED STATES PATENT AND TRADEMARK OFFICE
CERTIFICATE OF CORRECTION

PATENT NO. : 6,820,093 B2
DATED : November 16, 2004
INVENTOR(S) : Carlos De La Huerga It is certified that error appears in the above-identified patent and that said Letters Patent is hereby corrected as shown below:

Column 12,
Line 10, "$\#\#\#_{13}\#\#_{13}\#\#_{13}$", should be -- "$\#\#\#\_\#\#\_\#\#\_$" --.

Column 19,
Line 49, "out a" should be -- out in a --.

Column 38,
Lines 48 and 51, "records" should be -- record --.
Line 66, "segment" should be -- segments --.

Column 40,
Line 12, "code" should be -- coded --.
Line 33, "form" should be -- from --.
Line 43, "a action" should be -- an action --.

Column 41,
Line 6, "code" should be -- codes --.
Line 10, "to first" should be -- to the first --.

Column 42,
Line 56, "characteristic" should be -- characteristics --.

Signed and Sealed this

Nineteenth Day of April, 2005

JON W. DUDAS
*Director of the United States Patent and Trademark Office*